United States Patent [19]
Yew et al.

[11] Patent Number: 6,066,626
[45] Date of Patent: May 23, 2000

[54] COMPOSITIONS AND METHOD FOR TREATING LYSOSOMAL STORAGE DISEASE

[75] Inventors: Nelson S. Yew, West Upton; Robin J. Ziegler, Sterling; Seng H. Cheng, Wellesley, all of Mass.

[73] Assignee: Genzyme Corporation, Cambridge, Mass.

[21] Appl. No.: 09/182,245

[22] Filed: Oct. 29, 1998

Related U.S. Application Data

[60] Provisional application No. 60/063,527, Oct. 29, 1997.

[51] Int. Cl.$^7$ .................................................. A01N 43/04
[52] U.S. Cl. .................... 514/44; 435/208; 435/320.1; 435/325; 435/183; 424/93.1; 424/94.61
[58] Field of Search ............................... 424/94.61, 93.1; 514/44; 435/208, 320.1, 183

[56] References Cited

U.S. PATENT DOCUMENTS

| | | | |
|---|---|---|---|
| 5,580,757 | 12/1996 | Desnick et al. | 435/69.7 |
| 5,658,567 | 8/1997 | Calhoun et al. | 424/94.61 |
| 5,670,488 | 9/1997 | Gregory et al. | 514/44 |
| 5,783,565 | 7/1998 | Lee et al. | 514/44 |
| 5,911,983 | 6/1999 | Barranger et al. | 435/320.1 |
| 5,962,313 | 10/1999 | Podsakoff et al. | 424/93.21 |

OTHER PUBLICATIONS

Oshima et al., 1997, *Proc. Natl. Acad. Sci., USA* 94:2540–2544.
Bishop et al., 1986, *Proc. Natl. Acad. Sci., USA* 53:4859–4863.
Medin et al., 1996, *Proc. Natl. Acad. Sci., USA* 93:7917–7922.
Novo et al., 1997, *Gene Therapy* 4:488–492.
Sugimoto et al., 1995, *Human Gene Therapy* 6:905–915.
Ghodsi et al., 1998, *Human Gene Therapy* 9:2331–2340.
DePauly et al., 1998, *Gene Therapy* 5:473–480.
Desnick et al., in Scriver et al., eds. *The Molecular Basis of Inherited Disease*, 7$^{th}$ Ed., Chapter 89, pp. 2741–2784, 1995.
Cheng et al., 1998, Restoration of α–galactosidase Activity in Transgenic Fabry Mice by Gene Transfer Abstract published in Gene Therapy Meeting Abstract Book Jan. 14, 1998.
Takenaka T et al. Experimental Hematology 27:1149–59, 1999 (Abstract only).
Baker H et al. Federation Proceedings 35:1193–1201, 1982.

*Primary Examiner*—Bruce R. Campell
*Assistant Examiner*—Ram Shukla
*Attorney, Agent, or Firm*—Baker & Botts, LLP; Steven R. Lazar

[57] ABSTRACT

The present invention provides recombinant viral and non-viral vectors comprising a transgene encoding a biologically active human lysosomal enzyme that are able to infect and/or transfect and sustain expression of the biologically active human lysosomal enzyme transgene in mammalian cells deficient therein. In addition, methods are provided for providing a biologically active human lysosomal enzyme to cells deficient therein, which comprises introducing into the cells a vector comprising and expressing a transgene encoding the biologically active human lysosomal enzyme, wherein the vector is taken up by the cells, the transgene is expressed and biologically active enzyme is produced. The cells may be infected and/or transfected by the vector, dependent upon whether the vector is a viral vector and/or plasmid or the like. The invention also provides a method of supplying a biologically active human lysosomal enzyme to other distant cells deficient therein wherein the transfected and/or infected cells harboring the vector secrete the biologically active enzyme which is then taken up by the other deficient cells. In a preferred embodiment the present invention provides for sustained production of biologically human active α-galactosidase A in cells of Fabry individuals that are deficient in said enzyme.

14 Claims, 21 Drawing Sheets

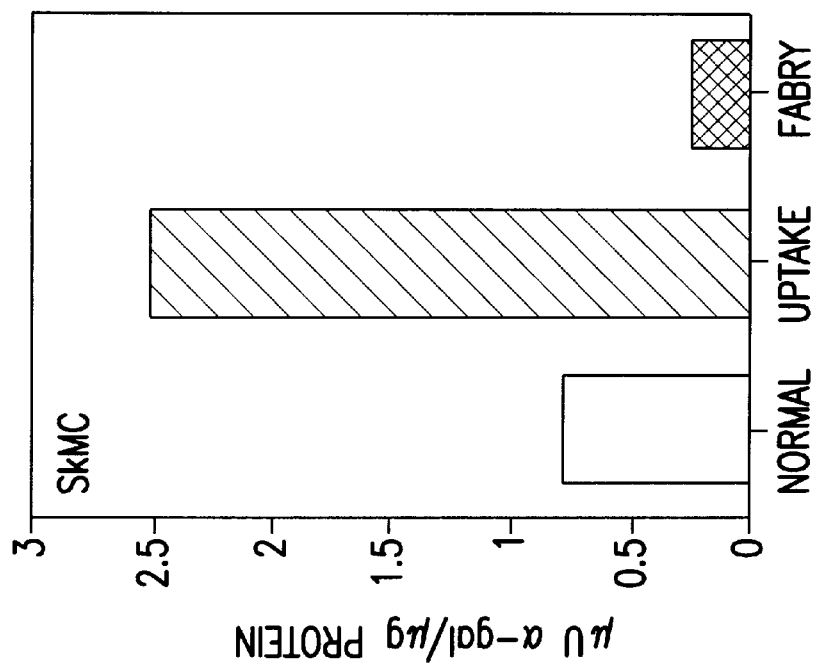
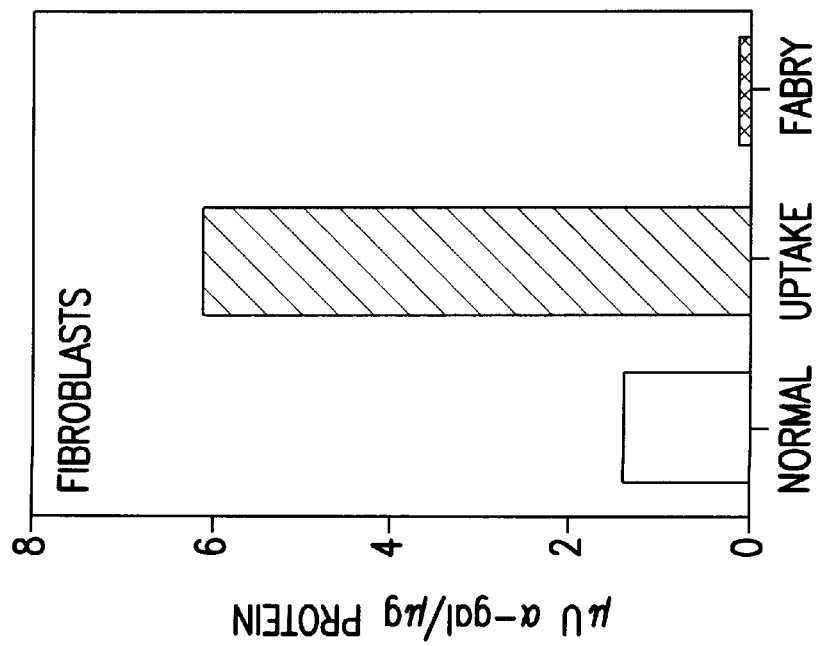

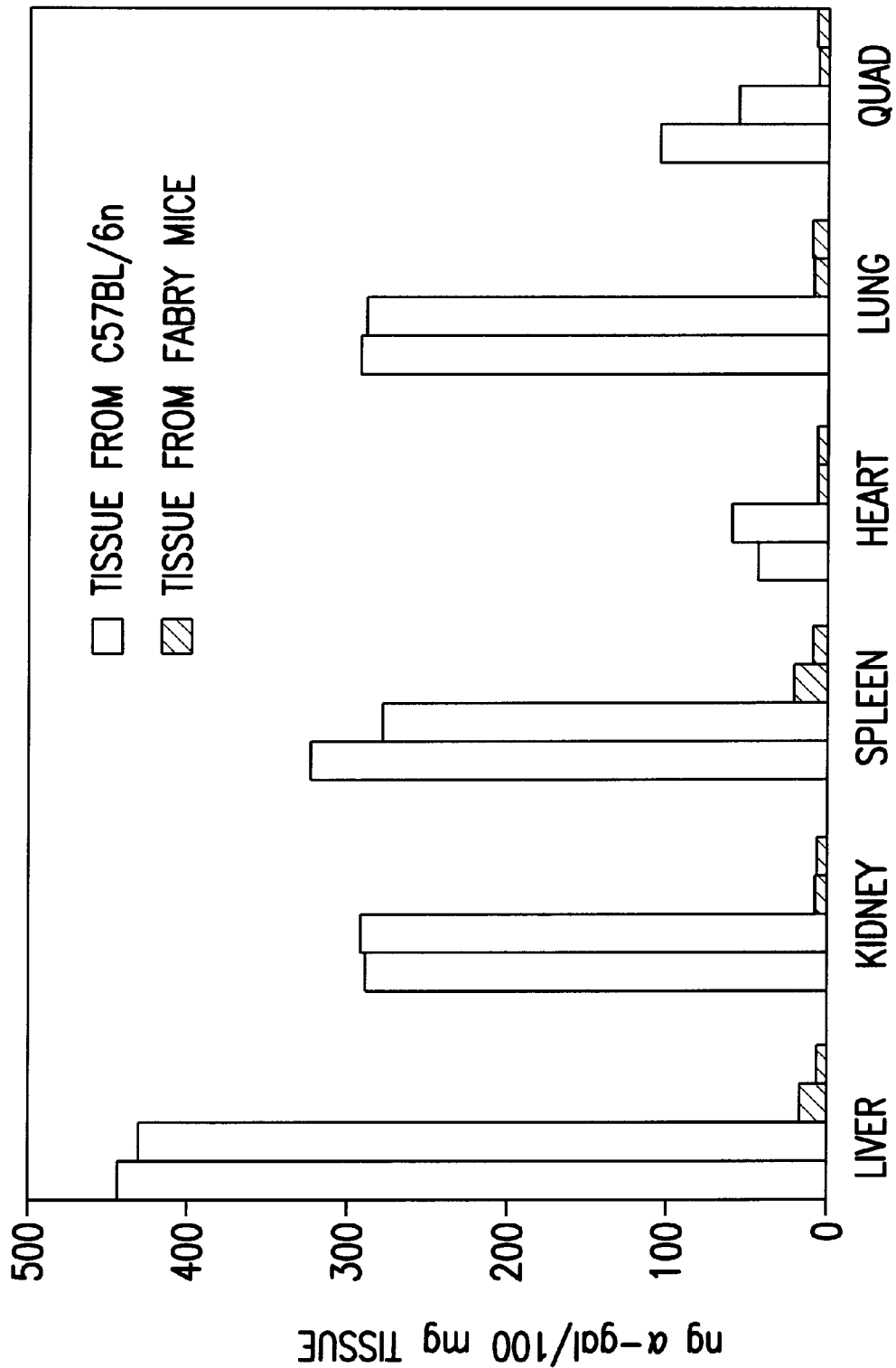

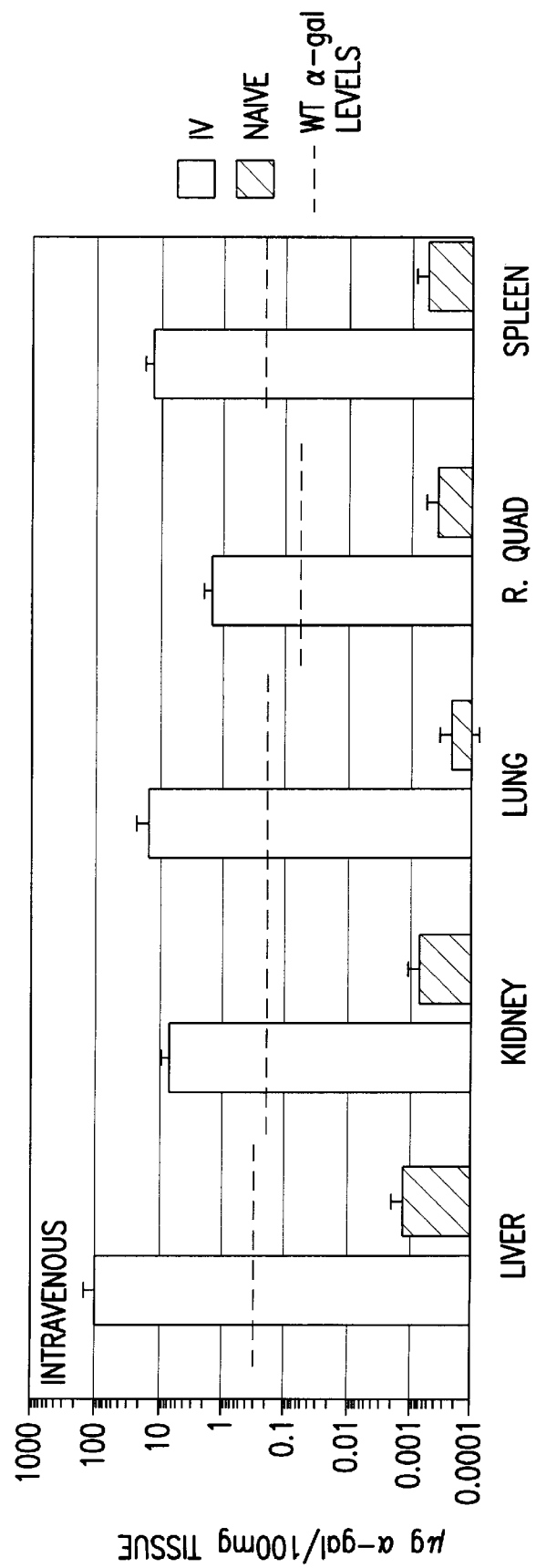

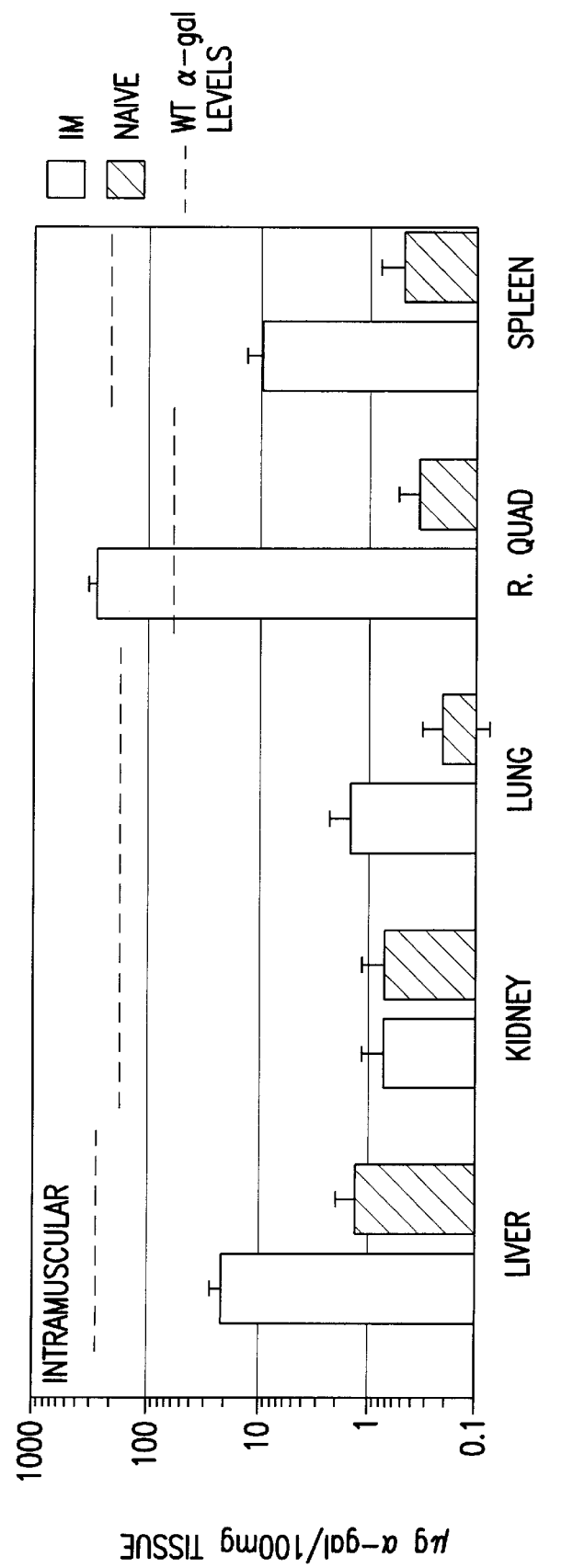

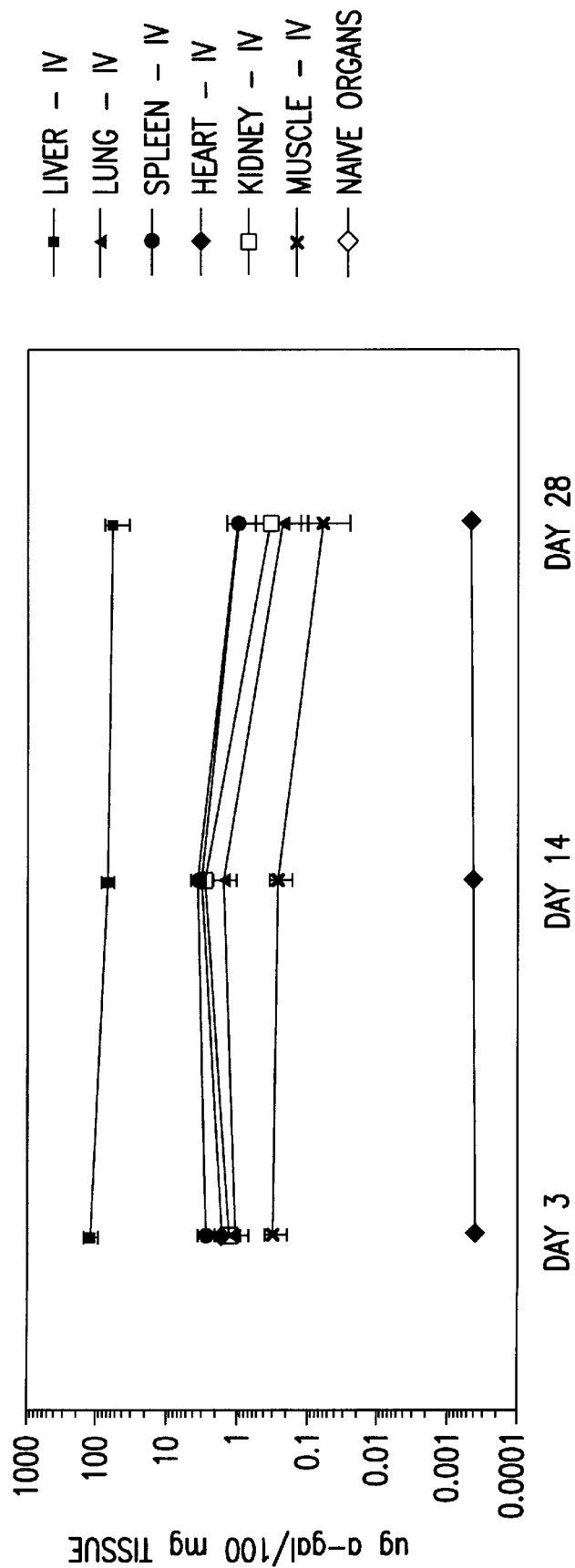

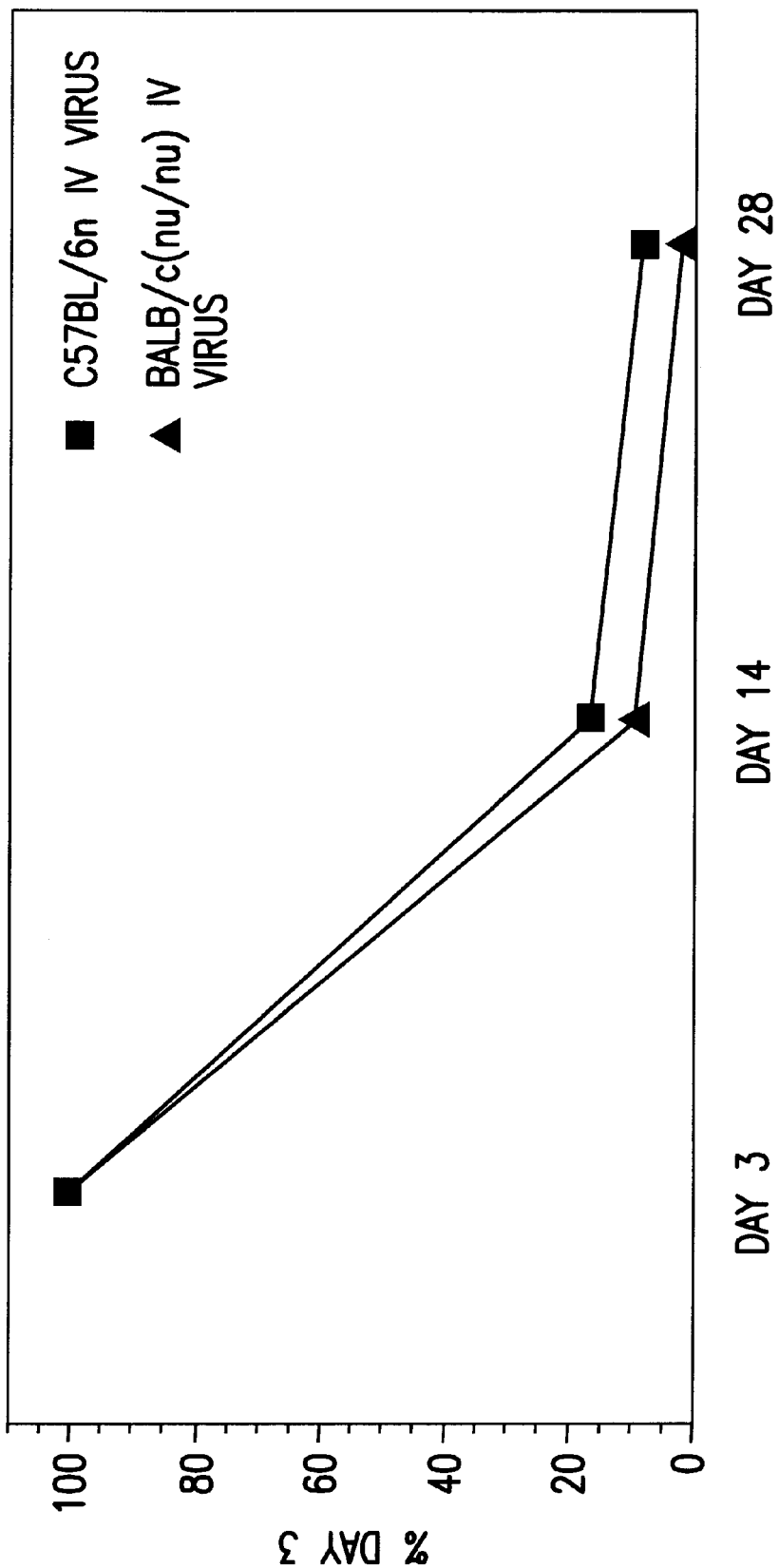

COMPOSITIONS AND METHOD FOR TREATING LYSOSOMAL STORAGE DISEASE

The present application is a continuation-in-part of U.S. Patent Application Serial No. 60/063,527 filed Oct. 29, 1997, the disclosure of which is incorporated herein by reference.

BACKGROUND OF THE INVENTION

Lysosomal storage diseases are a group of over 40 disorders which are the result of defects in genes encoding enzymes that break down glycolipid or polysaccharide waste products within the lysosomes of cells. The enzymatic products, e.g., sugars and lipids, are then recycled into new products. Each of these disorders results from an inherited autosomal or X-linked recessive trait which affects the levels of enzymes in the lysosome. Generally, there is no biological or functional activity of the affected enzymes in the cells and tissues of affected individuals. Table I provides a list of representative storage diseases and the enzymatic defect associated with the diseases. In such diseases the deficiency in enzyme function creates a progressive systemic deposition of lipid or carbohydrate substrate in lysosomes in cells in the body, eventually causing loss of organ function and death. The genetic etiology, clinical manifestations, molecular biology and possibility of the lysosomal storage diseases are detailed in Scriver et al., eds., *The Metabolic and Molecular Basis of Inherited Disease*, 7$^{th}$ Ed., Vol. II, McGraw Hill, (1995).

TABLE I

Lysosomal storage diseases and associated enzymatic defects

| Disease | Enzymatic Defect |
| --- | --- |
| Pompe disease | acid α-glucosidase (acid maltase) |
| MPSI* (Hurler disease) | α-L-iduronidase |
| MPSII (Hunter disease) | iduronate sulfatase |
| MPSIII (Sanfilippo) | heparan N-sulfatase |
| MPS IV (Morquio A) | galactose-6-sulfatase |
| MPS IV (Morquio B) | acid β-galactosidase |
| MPS VII (Sly disease) | β-glucoronidase |
| I-cell disease | N-acetylglucosamine-1-phosphotransferase |
| Schindler disease | α-N-acetylgalactosaminidase (α-galactosidase B) |
| Wolman disease | acid lipase |
| Cholestrol ester storage disease | acid lipase |
| Farber disease | lysosomal acid ceramidase |
| Niemann-Pick disease | acid sphingomyelinase |
| Gaucher disease | β-glucosidase (glucocerebrosidase) |
| Krabbe disease | galactosylceramidase |
| Fabry disease | α-galactosidase A |
| GM1 gangliosidosis | acid β-galactosidase |
| Galactosialidosis | β-galactosidase and neuraminidase |
| Tay-Sach's disease | hexosaminidase A |
| Sandhoff disease | hexosaminidase A and B |

*MPS = mucopolysaccaridosis

As a representative of the class of lysosomal storage diseases, Fabry Disease is a recessive, X-linked inherited recessive disorder caused by a deficiency in the lysosomal enzyme α-galactosidase A. Absence of this lysosomal hydrolase results in progressive deposition of the glycosphingolipid globotriasylceramide (GL3), or galactosyl-(α1->4)-galactosyl-(β1->4)-glucosyl-(β1->1')-ceramide, in most tissues of the body. The birefringent deposits of GL3 are primarily found in the vascular endothelium. Progressive endothelial accumulation of GL3, leads to ischemia and infarction in organs such as kidney, heart or brain, causing excruciating pain, kidney failure, cardiac and cerebrovascular disease. The average age of death for an affected individual, from renal, cardiac and/or cerebral complications of the vascular disease, is 41 years. There are no effective treatments currently available for this disease. (See, e.g., Desnick et al., in Scriver et al., eds. *The Molecular Basis of Inherited Disease*, 7$^{th}$ Ed., Chapter 89, pp.2741–2784, McGraw Hill (1995)).

Human α-galactosidase A (α-D-galactoside galactohydrolase; α-gal A; EC 3.2.1.22) is a lysosomal exoglycosidase encoded by a gene on Xq22. A human liver cDNA that codes for α-galactosidase A was isolated from a λgt11 expression library (Calhoun et al., *Proc. Natl. Acad. Sci., USA* 82:7364–7368 (1985)). The isolated cDNA encoded the mature amino acid sequence of α-galactosidase A but did not contain the complete signal peptide sequence of the precursor form (Bishop et al., *Proc. Natl. Acad. Sci., USA* 83:4859–4863 (1986). This partial cDNA clone was then used to construct an *E. coli* expression vector with the α-galactosidase A coding sequence under control of the trp promoter (Hantzopoulos et al., *Gene* 57:159–169 (1987)). A genomic clone was later isolated which carried the promoter and first exon of the protein including the full signal peptide (Quinn et al., *Gene* 58:177–188 (1987)). Further, full length cDNA clones isolated from human fibroblasts were obtained and used to obtain transient expression of α-galactosidase A in COS cells (Tsuji et al., *Eur. J. Biochem.* 165:275–280 (1987)). Recently, a Fabry knockout transgenic mouse demonstrating a deficiency in this enzyme activity has been made (Ohshima et al., *Proc. Natl. Acad. Sci., USA* 94:2540–2544 (1997) knockout mice display a complete lack of α-galactosidase A activity). Lipid analysis of the liver and kidneys of the knockout mice revealed a marked accumulation of GL3 over time, indicating the similarity of the pathophysiological process in the mutant mice and in patients with Fabry disease. Id. Thus, the Fabry knockout mice provide an excellent model for the human disease.

De Duve first suggested that replacement of the missing lysosomal enzyme with exogenous biologically active enzyme might be a viable approach to treatment of lysosomal storage diseases. De Duve, *Fed Proc.* 23:1045 (1964). Since that time, various studies have suggested that enzyme replacement therapy may be beneficial for treating various lysosomal storage diseases. The best success has been shown with individuals with type I Gaucher disease, who have been treated with exogenous enzyme (β-glucocerebrosidase), prepared from placenta (Ceredase®) or, more recently, recombinantly (Cerezyme®). It has been suggested that enzyme replacement may also be beneficial for treating Fabry's disease, as well as other lysosomal storage diseases. See, for example, Dawson et al., *Ped. Res.* 7(8):684–690 (1973) (in vitro) and Mapes et al., *Science* 169:987 (1970) (in vivo). Clinical trials of enzyme replacement therapy have been reported for Fabry patients using infusions of normal plasma (Mapes et al., *Science* 169:987–989 (1970)); α-galactosidase A purified from placenta (Brady et al., *N. Eng.J.Med.* 279:1163 (1973)); or α-galactosidase A purified from spleen or plasma (Desnick et al., *Proc. Natl. Acad. Sci., USA* 76:5326–5330 (1979)) demonstrated the biochemical effectiveness of direct enzyme replacement for Fabry disease. These studies indicated the potential for eliminating, or significantly reducing, the pathological glycolipid storage by repeated enzyme replacement. For example, in one study (Desnick et al., supra), intravenous injection of purified enzyme resulted in a transient reduction in the plasma levels of the stored lipid substrate, globotriasylceramide.

However, to date, the biochemical and clinical effectiveness of enzyme replacement in Fabry disease, as well as other lysosomal storage diseases, has not been demonstrated due to the lack of sufficient human enzyme for adequate doses and long-term evaluation.

Accordingly, there exists a need in the art for methods for providing sufficient quantities of biologically active lysosomal enzymes, such as human α-galactosidase A, to deficient cells. Additionally, there exists a need for new vector compositions that allow for efficient transfer of genes encoding lysosomal enzymes, such as α-galactosidase A, to deficient cells and at the same time direct expression of the transferred gene. Recently, recombinant approaches have attempted to address these needs, see, e.g., U.S. Pat. No. 5,658,567 issued Aug. 19, 1997 for Recombinant alpha-galactosidase A therapy for Fabry disease; U.S. Pat. No. 5,580,757 issued Dec. 3, 1996 for Cloning and Expression of Biologically Active alpha-galactosidase A as a Fusion Protein; Bishop, D. F. et al., *Proc. Natl. Acad Sci., USA*. 83:4859–4863, (1986); Medin, J. A. et al., *Proc. Natl. Acad. Sci., USA*. 93:7917–7922, (1996); Novo, F. J., *Gene Therapy*. 4:488–492, (1997); Ohshima, T. et al., *Proc. Natl. Acad. Sci., USA*. 94:2540–2544, (1997); and Sugimoto Y. et al., *Human Gene Therapy*. 6:905–915, (1995). In addition, in allowed U.S. patent application Ser. No. 08/466,597, filed Jun. 6, 1995, incorporated herein by reference, retroviral expression vectors containing a gene encoding human β-glucocerebrosidase were shown to infect autologous hematopoietic stem cells, which when retransplanted into a Gaucher patient provided sustained production of biologically active enzyme to the patient.

To date, however, there has not been a vector composition that has proven capable of transducing and sustaining expression of the human β-galactosidase A gene, or most other genes encoding lysosomal enzymes to cells that are deficient therein. The present invention satisfies these needs and provides related advantages as well.

SUMMARY OF THE INVENTION

Accordingly, the present invention provides recombinant viral and non-viral vectors comprising a transgene encoding a biologically active human lysosomal enzyme that are able to infect and/or transfect and sustain expression of the biologically active human lysosomal enzyme transgene in mammalian cells deficient therein. In a preferred embodiment, the expressed transgene encodes α-galactosidase and the deficient cells are those of an individual with Fabry's disease.

The present invention further provides a method for providing a biologically active human lysosomal enzyme to cells deficient therein, which comprises introducing into the cells a vector comprising and expressing a transgene encoding the biologically active human lysosomal enzyme, wherein the vector is taken up by the cells, the transgene is expressed and biologically active enzyme is produced. The cells may be infected and/or transfected by the vector, dependent upon whether the vector is a viral vector and/or plasmid or the like.

In a preferred embodiment the present invention provides for sustained production of biologically human active α-galactosidase A in cells of Fabry individuals that are deficient in said enzyme.

In a still further aspect, the invention also provides a method of supplying a biologically active human lysosomal enzyme to other distant cells deficient therein wherein the transfected and/or infected cells harboring the vector secrete the biologically active enzyme which is then taken up by the other deficient cells. In a preferred embodiment, the enzyme is human α-galactosidase A and the cells are those of a Fabry individual.

In a still further aspect, the biologically active enzyme, preferably α-galactosidase A, is secreted into the circulation of an individual (e.g., a Fabry individual).

The present invention also provides a recombinant E1 deleted adenoviral vector, Ad2/CEHα-gal, and a recombinant plasmid expression vector, pCFA-hAGA, both of which comprised and express a transgene encoding α-galactosidase A.

The present invention further provides a method for providing biologically active human α-galactosidase A to the cells of an individual with Fabry disease comprising introducing into the cells of a Fabry individual an amount of Ad2/CEHα-gal effective to infect and sustain expression of the biologically active human α-galactosidase A transgene in cells deficient therein.

The present invention further provides a method for providing biologically active human α-galactosidase A to the cells of an individual with Fabry disease comprising introducing into the cell of a Fabry individual an amount of pCFA-hAGA effective to transfect and sustain expression of biologically active human α-gal A gene in cells deficient therein.

Other features and advantages of the present invention will be apparent from the following detailed description as well as from the claims.

BRIEF DESCRIPTION OF THE DRAWINGS

FIGS. 3A–3B show uptake of α-galactosidase A produced from Ad2/CEHα-gal by Fabry cells. FIG. 3A shows uptake of α-galactosidase A expressed in Ad2/CEHα-gal infected fibroblasts (GM02775). FIG. 3B shows uptake of α-galactosidase A expressed in Ad2/CEHα-gal infected skeletal muscle cells (SkMC).

FIG. 4 shows tissue distribution of α-galactosidase A in normal vs. Fabry's knockout mice.

FIGS. 6A–6B show tissue distribution of α-galactosidase A after administration of Ad2/CEHα-gal/CEHα-gal vector to Fabry's knockout mice. FIG. 6A shows distribution after viral injection into the tail vein of female Fabry's knockout mice. FIG. 6B shows distribution after viral injection into the right quadriceps muscle group of female Fabry's mice.

FIGS. 7A–7B show a time course of α-galactosidase A expression after intravenous injection of Ad2/CEHα-gal into C57BL/6n mice. FIG. 7A shows expression of α-galactosidase A over time. FIG. 7B shows persistence of α-galactosidase A relative to day 3.

FIGS. 8A–8B show levels of α-galactosidase A in whole blood after intravenous injection of Ad2/CEHα-gal into C57BL/6n and BALB/c(nu/nu) mice. FIG. 8A shows expression of α-galactosidase A over time. FIG. 8B shows persistence of α-galactosidase A relative to day 3.

FIG. 9A shows a α-galactosidase A expression over time. FIG. 9B shows persistence of α-galactosidase A relative to day 3.

FIG. 10A shows a α-galactosidase A expression over time. FIG. 10B shows persistence of α-galactosidase A relative to day 3.

DETAILED DESCRIPTION OF THE INVENTION

Figure 1:
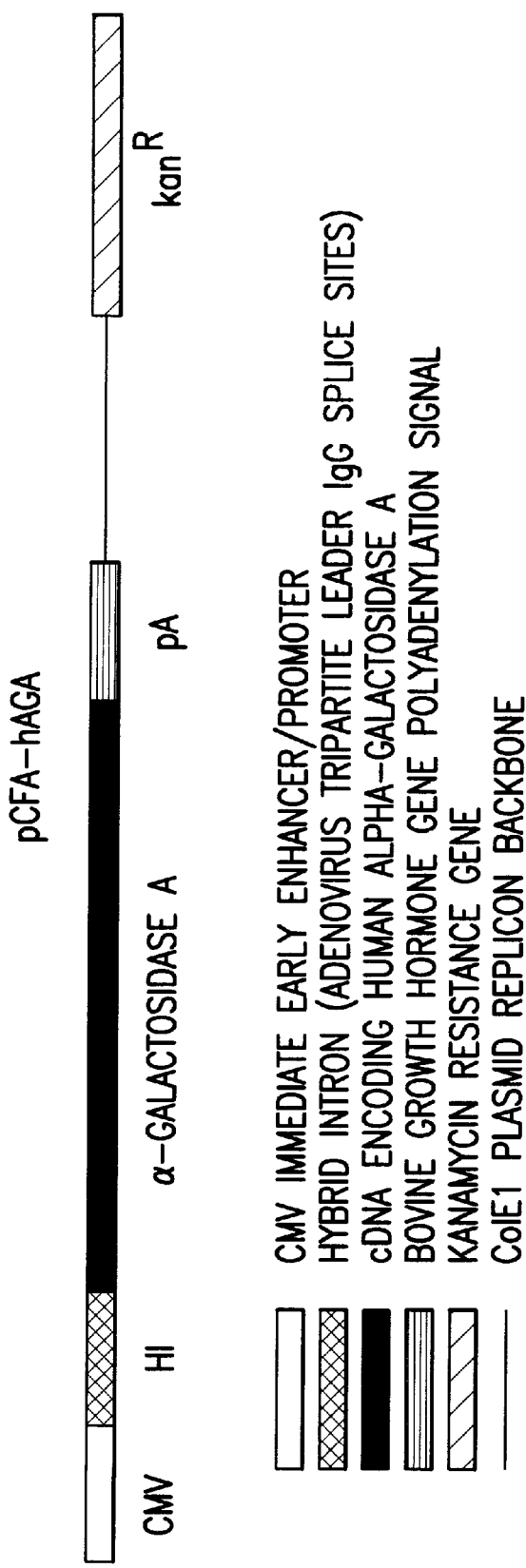
FIG. 1 shows the plasmid expression vector pCFA-hAGA.

The present invention provides recombinant viral and non-viral vectors comprising a transgene encoding a biologically active human lysosomal enzyme that are able to infect and/or transfect and sustain expression of the biologically active human lysosomal enzyme transgene in mammalian cells deficient therein. In a preferred embodiment, the expressed transgene encodes α-galactosidase A.

The present invention further provides a method for providing a biologically active human lysosomal enzyme to cells deficient therein which comprises introducing into the cells a vector comprising and expressing a transgene encoding the biologically active human lysosomal enzyme, wherein the vector is taken up by the cells, the transgene is expressed and biologically active enzyme is produced. The cells may be infected and/or transfected by the vector, dependent upon whether the vector is a viral vector and/or plasmid or the like.

In a still further aspect, the invention provides a method of supplying a biologically active human lysosomal enzyme to other distant cells deficient therein wherein the transfected and/or infected cells harboring the vector secrete the biologically active enzyme which is then taken up by the other deficient cells.

Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression.

Polynucleotides/transgenes are inserted into vector genomes using methods well known in the art. Transgenes are defined herein as nucleic acids molecules or structural genes that encode a particular protein—in the present invention, a human lysosomal enzyme and nucleic acids encoding said enzymes. Representative lysosomal enzymes in accordance with the present invention are provided in Table I above. References relating to isolation and characterization of the lysosomal enzymes in Table I may be found in Scriver et al., *The Metabolic Basis of Inherited Disease,* 7$^{th}$ Ed., vol. 11, pp. 2427–2879, McGraw Hill (1995), incorporated herein by reference.

By way of example, in order to insert the transgene into the vector, transgene and vector nucleic can be contacted, under suitable conditions, with a restriction enzyme to create complementary ends on each molecule that can pair with each other and be joined together with a ligase. Alternatively, synthetic nucleic acid linkers can be ligated to the termini of the restricted polynucleotide. These synthetic linkers contain nucleic acid sequences that correspond to a particular restriction site in the vector nucleic acid. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

As used herein, "expression" refers to the process by which polynucleotides/transgenes are transcribed into mRNA and then translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al., *Molecular Cloning, A Laboratory Manual* 2d Ed. (Cold Spring harbor, N.Y., 1989), or Ausubel et al., *Current Protocols in Molecular Biology* (Greene Assoc., Wiley Interscience, New York, N.Y., 1995). Similarly, a eukaryotic expression vector, be it a virus or a plasmid, includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general. Expression vectors are useful to produce cells that express the protein encoded by the polynucleotide/transgene.

Preparations of the transgene encoding a human lysosomal enzyme, e.g., α-galactosidase A, can be incorporated in a suitable vector for delivery into an individual's cells, e.g., a Fabry individual, using methods that are known in the art. See, for example, Finkel and Epstein, *FASEB J.* 9:843–851 (1995); Feldman and Steg, *Cardiovascular Res.* 32:194–207 (1996).

Naked nucleic—Naked plasmid DNA can be introduced into muscle cells, for example, by direct injection into the tissue. (Wolff et al., *Science* 247:1465 (1989)).

Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, *Nature* 337:387 (1989)). Intravenous injection of cationic lipid-plasmid complexes into mice has been shown to result in expression of the DNA in lung (Brigham et al., *Am. J. Med. Sci.* 298:278 (1989)). See also, Osaka et al.,*J. Pharm. Sci.* 85(6):612–618 (1996); San et al., *Human Gene Therapy* 4:781–788 (1993); Senior et al., *Biochemica et Biophysica Acta* 1070:173–179 (1991); Kabanov and Kabanov, *Bioconjugate Chem.* 6:7–20 (1995); Remy et al., *Bioconjugate Chem.* 5:647–654 (1994); Behr, J-P., *Bioconjugate Chem* 5:382–389 (1994); Behr et al., *Proc. Natl. Acad. Sci., USA* 86:6982–6986 (1989); and Wyman et al., *Biochem.* 36:3008–3017 (1997).

Cationic are known to those of ordinary skill in the art. Representative cationic lipids include those disclosed, for example, in U.S. Pat. No. 5,283,185 ; and e.g., U.S. Pat. No. 5,767,099, the disclosures of which are incorporated herein by reference. In a preferred embodiment, the cationic lipid is $N^4$-spermine cholesteryl carbamate (GL-67) disclosed in U.S. Pat. No. 5,767,099. Additional preferred lipids include $N^4$-spermidine cholestryl carbamate (GL-53) and 1-($N^4$-spermind) -2,3-dilaurylglycerol carbamate (GL-89 )

Adenovirus—Adenovirus-based vectors for the delivery of transgenes are well known in the art and may be obtained commercially or constructed by standard molecular biological methods. Recombinant adenoviral vectors containing exogenous genes for transfer are, generally, derived from adenovirus type 2 (Ad2) and adenovirus type 5 (Ad5). They may also be derived from other non-oncogenic serotypes. See, for example, Horowitz, "Adenoviridae and their Replication" in *VIROLOGY*, 2d ed., Fields et al. Eds., Raven Press Ltd., New York, 1990, incorporated herein by reference.

The adenoviral vectors of the present invention are incapable of replicating, have minimal viral gene expression and are capable of expressing a transgene in target cells. Adenoviral vectors are generally rendered replication-defective by deletion of the E1 region genes. The replication-defective vectors maybe produced in the 293 cell line (ATCC CRL 1573), a human embryonic kidney cell line expressing E1 functions. The deleted E1 region may be replaced by the transgene of interest under the control of an adenoviral or non-adenoviral promoter. The transgene may also be placed in other regions of the adenovirus genome. See, Graham et al., "Adenovirus-based Expression Vectors and Recombinant Vaccines" in *VACCINES: NEW APPROACHES to IMMUNOLOGICAL PROBLEMS* pp363–390, Ellis, Ed., Butterworth-Heinemann, Boston, (1992) for a review of the production of replication-defective adenoviral vectors, also incorporated herein by reference.

Skilled artisans are also aware that other non-essential regions of the adenovirus can be deleted or repositioned within the viral genome to provide an adenoviral vector suitable for delivery of a transgene in accordance with the present invention. For example, U.S. Pat. No. 5,670, 488, incorporated herein by reference, discloses that some or all of the E1 and E3 regions may be deleted, and non-essential open reading frames (ORFs) of E4 not required for in vitro virus propagation can also be deleted. Other representative adenoviral vectors are disclosed, for example, by Rich et al., *Human Gene Therapy* 4:461 (1993); Brody et al., *Ann. NYA cad. Sci.* 716:90 (1994); Wilson, *N. Eng. J. Med.* 334:1185 (1996); Crystal, *Science* 270:404 (1995); O'Neal et al., *Hum. Mol. Genet.* 3:1497 (1994); and Graham et al., supra., incorporated herein by reference. In a preferred embodiment of the present invention, the adenoviral vector is an E1 deleted Ad2-based vector, e.g. as disclosed in U.S. Pat. No. 5,670,488, incorporated herein by reference. Other adenoviral vectors that may be used include those that have been designed to prevent the generation of replication competent adenovirus in vivo (U.S. Pat. No. 5,707,618, incorporated herein by reference). In addition, pseudoadenovirus vectors (PAV), which are deleted for early and late genes, as disclosed in U.S. Pat. No. 5,670,488, are also contemplated for use herein.

As defined above, a transgene, as used herein, is a nucleic acid or structural gene coding for a human lysosomal enzyme. Moreover the transgene is foreign or non-native to adenovirus. Any nucleic acid coding for a human lysosomal enzyme that can be transcribed in the adenoviral vector is contemplated. In a preferred embodiment, the transgene encodes a biologically active or functional α-galactosidase A protein. A biologically active or functional protein or peptide is a protein or peptide that affects the cellular mechanism of a cell in which it is expressed, or the function of a tissue or organism. In the case of α-galactosidase A, the enzyme cleaves the lipid substrate globotriasylceramide (galactosyl-galactosyl-glucosyl-ceramide) or GL3.

In the adenoviral vectors of the present invention, the transgene is operably linked to expression control sequences, e.g., a promoter that directs expression of the transgene. As used herein, the phrase "operatively linked" refers to the functional relationship of a polynucleotide/ transgene with regulatory and effector sequences of nucleotides, such as promoters, enhancers, transcriptional and translational stop sites, and other signal sequences. For example, operative linkage of a nucleic acid to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide.

Promoter regions include specific sequences that are sufficient for RNA polymerase recognition, binding and transcription initiation. Additionally, promoter regions include sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals. In particular, the use of a CMV promoter/transgene, together with adenovirus E4 region, preferably ORF3, which as disclosed in PCT/US98/07841, filed Apr. 14, 1998 and incorporated herein by reference, has been shown to provide increased persistence of transgene expression is preferred. Also, E1 deleted, partially E3 deleted vectors capable of providing persistent expression of a transgene, as disclosed in PCT/US98/07840, filed Apr. 14, 1998 and incorporated herein by reference, are also contemplated.

Other viral vectors for use in the present invention include vectors derived from vaccinia, herpesvirus, AAV and retroviruses. In particular, herpesviruses, especially herpes simplex virus (HSV), such as those disclosed in U.S. Pat. No. 5,672,344, the disclosure of which is incorporated herein by reference, are particularly useful for delivery of a transgene to a neuronal cell, which has importance for those lysosomal storage diseases in which the enzymatic defect manifests in neuronal cells, e.g, Hurler's, Hunter's, and Tay-Sach's diseases. AAV vectors, such as those disclosed in U.S. Pat. Nos. 5,139,941, 5,252,479 and 5,753,500 and PCT publication WO 97/09441, the disclosures of which are incorporated herein, are also useful since these vectors integrate into host chromosomes, with a minimal need for repeat administration of vector.

Retroviruses may also find use in the present invention, especially for transgene delivery to cells that can be removed from an individual, infected ex vivo and readministered back to the individual for production of biologically active enzyme.

The viral and non-viral vectors of the present invention are useful for transferring a transgene encoding a lysosomal enzyme to a target cell. The target cell may be in vitro or in vivo. Use of invention vectors in vitro allows the transfer of a transgene to a cultured cell and is useful for the recombinant production of the transgene product. Use of invention vectors to deliver a transgene to a cell in vivo is useful for providing biologically active enzyme to cells deficient therein, for example, in the case of Fabry disease, a cell in which α-galactosidase A is absent, insufficient or nonfunctional.

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule. The ability of targeted vectors renders invention vectors particularly useful in the treatment of lysosomal storage disorders. For example, including a targeting molecule, such as VEGF or an antibody to a VEGF receptor can provide targeting to vascular endothelial cells in individuals with Fabry's disease.

In addition, viral vectors, especially adenoviral vectors that have been complexed with a cationic amphiphile, such as a cationic lipid as described above, polyL-lysine (PLL), and diethylaminoethyldextran (DELAE-dextran) provide increased inefficiency of viral infection of target cells (See, e.g., PCT/US97/21496 filed Nov. 20, 1997, incorporated herein by reference).

Adenoviral vectors complexed with DEAE dextran are particularly preferred. In addition, since repeat administration of a viral vector can result in an immune response to the vector, thereby limiting its effectiveness in delivering the gene to affected cells, adenovirus and other viral vectors may be polymer-modified, e.g. complexed with polyethylene glycol (PEG), to reduce viral immunogenicity and allow for repeat administration of the vector (See, e.g., PCT/US98/06609 filed Apr. 3, 1998, incorporated herein by reference). Alternatively, the vector may be administered with an immunosuppressive agent to reduce the immune response to repeated vector administration. In addition, combinations of the above approaches may be used.

Transfer of the transgene to the target cells by invention vectors can be evaluated by measuring the level of the transgene product (biologically active enzyme) in the target cell. The level of transgene product in the target cell directly correlates with the efficiency of transfer of the transgene by invention vectors. Any method known in the art can be used to measure enzyme levels, such as ELISA, radioimmunoassay, assays using an fluorescent and chemiluminescent enzyme substrates.

Expression of the transgene can be monitored by a variety of methods known in the art including, inter alia, immunological, histochemical and activity assays. Immunological procedures useful for in vitro detection of the transgene product in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides. enzymes, fluorogens, chromogens and chemiluminescent labels.

For in vivo imaging methods, a detectable antibody can be administered to a subject and the binding of the antibody to the transgene product can be detected by imaging techniques well known in the art. Suitable imaging agents are known and include, for example. gamma-emitting radionuclides such as $^{111}$In, $^{99m}$Tc, $^{51}$Cr and the like, as well as paramagnetic metal ions, which are described in U.S. Pat. No. 4,647,447. The radionuclides permit the imaging of tissues by gamma scintillation photometry, positron emission tomography, single photon emission computed tomography and gamma camera whole body imaging, while paramagnetic metal ions permit visualization by magnetic resonance imaging.

The present invention is exemplified using vectors comprising an α-galactosidase A transgene to deliver biologically active α-galactosidase A to cells and tissues of individuals with Fabry's disease. The efficacy of this approach has been demonstrated using a mouse model system, e.g., a Fabry knockout mouse. Thus, active human α-galactosidase A is provided to the cells of an individual with Fabry disease by introducing into a Fabry individual an amount of invention vectors effective to infect and/or transfect and sustain expression of biologically active human α-gal A gene in cells deficient therein. Invention vectors may be delivered to the target cells in a suitable composition, either alone, or complexed, as provided above, comprising the vector and a suitably acceptable carrier. Plasmid vectors are preferably complexed with a cationic lipid such as GL67. Adenoviral vectors are preferably complexed with DEAE dextran. The vector may be delivered to target cells by methods known in the art, for example, intravenous, intramuscular, intranasal, subcutaneous, intubation, lavage, and the like.

The terms transgene encoding α-galactosidase A includes a nucleic acid (DNA) or a structural gene that encodes α-galactosidase A that, when expressed in deficient cells of a Fabry individual, alleviate the α-galactosidase A deficiency therein.

As used herein the terms effective amount refers to an amount that alleviates the deficiency by the production of biologically active α-galactosidase A in the cells of a Fabry individual. Production of biologically active α-galactosidase A in Fabry individuals can be evaluated by the alleviation of the symptoms associated with Fabry disease. The precise effective amount of vector to be used in the method of the present invention can be determined by one of ordinary skill in the art with consideration of, for example, individual differences in age, weight, extent of disease and condition of the individual.

In particular, the present invention provides both viral and non-viral approaches for delivering biologically active α-galactosidase A to cells of individuals with Fabry disease. A recombinant adenoviral vector (pAd2/CEHα-gal) and a plasmid expression vector (pCFA-hAGA) that express human α-galactosidase A (α-gal) have been constructed. A human airway epithelial cell line that was either infected or transfected with these vectors expressed active enzyme at levels more than a log higher than endogenous levels, with a significant proportion of the activity being secreted into the medium. The α-galactosidase A secreted from either infected fibroblasts (GM02775) or infected primary human skeletal muscle cells (SkMC) was shown to be taken up by Fabry fibroblasts. This indicates that enzyme can be secreted by cells that have taken up the vector in vivo, and that the secreted enzyme can be taken up by untransfected cells, thus correcting the genetic defect in a large percentage of cells in the body.

Studies have been undertaken in mice using pCFA-hAGA to compare the efficacy of three potential routes of delivery—intranasal, intravenous, and intramuscular administration. Intranasal instillation into the lung of plasmid DNA complexed with the cationic lipid GL-67 resulted in low level expression (up to 1800 pg α-gal per 100 mg tissue) in the lung. Intravenous administration of plasmid DNA complexed with lipid GL-67 also showed low levels of expression in the lung (up to 700 pg per 100 mg tissue). Intramuscular injection of plasmid DNA alone in the absence of cationic lipid produced low levels of expression (up to 1200 pg per 100 mg tissue) in the injected muscle. Experiments performed using the adenovirus vector show very high levels of activity in all of the tissues assayed (up to 100 µg per 100 mg tissue in the liver, 10 µg per 100 mg tissue in most other organs). The level of enzyme assayed in liver from normal mice was 400 ng per 100 mg tissue. The tissue samples from the virus treated mice were assayed by two different methods, an activity assay and an ELISA assay, with similar results.

In addition, intravenous administration of viral vectors to Fabry mice has been shown to result in a decrease in accumulated GL3 substrate in a wide variety of tissues in treated animals. It has been shown that small quantities of lysosomal enzymes are normally secreted and that these can be recaptured by distant cells through the mannose-6-phosphate receptors. Indeed, the results presented show that α-galactosidase A collected from supernatants of cells transfected with viral and non-viral vectors encoding the enzyme are capable of being internalized by Fabry cells. These results further suggest that gene transfer of α-galactosidase A to an appropriate depot organ can facilitate reversion of the biochemical defect and storage of GL3 in the affected tissues of Fabry patients.

The present invention is further illustrated by the following examples which in no way should be construed as being further limiting. The contents of all references cited throughout this application are hereby expressly incorporated by reference.

EXAMPLES

Example 1

Vector Construction pCFA-hAGA

This plasmid expression vector utilizes the cytomegalovirus immediate early promoter to drive expression of the human α-galactosidase A cDNA. A hybrid intron was included after the promoter to provide splice sites to enhance expression. The polyadenylation signal was taken from the bovine growth hormone gene. The ColE1 replicon from pUC was used as a backbone for replication in *E. coli*. The kanamycin resistance gene was used to select for plasmid maintenance. The construction of the pCFA-hAGA is analogous to the construction of the pCF1 vector containing a CFTR transgene disclosed, e.g., in U.S. Pat. No. 5,783,565, the disclosure of which is incorporated herein by reference. In the pCFA-hAGA vector, an α-galactosidase A transgene is substituted for the CFTR transgene in pCFI.

Figure 2:
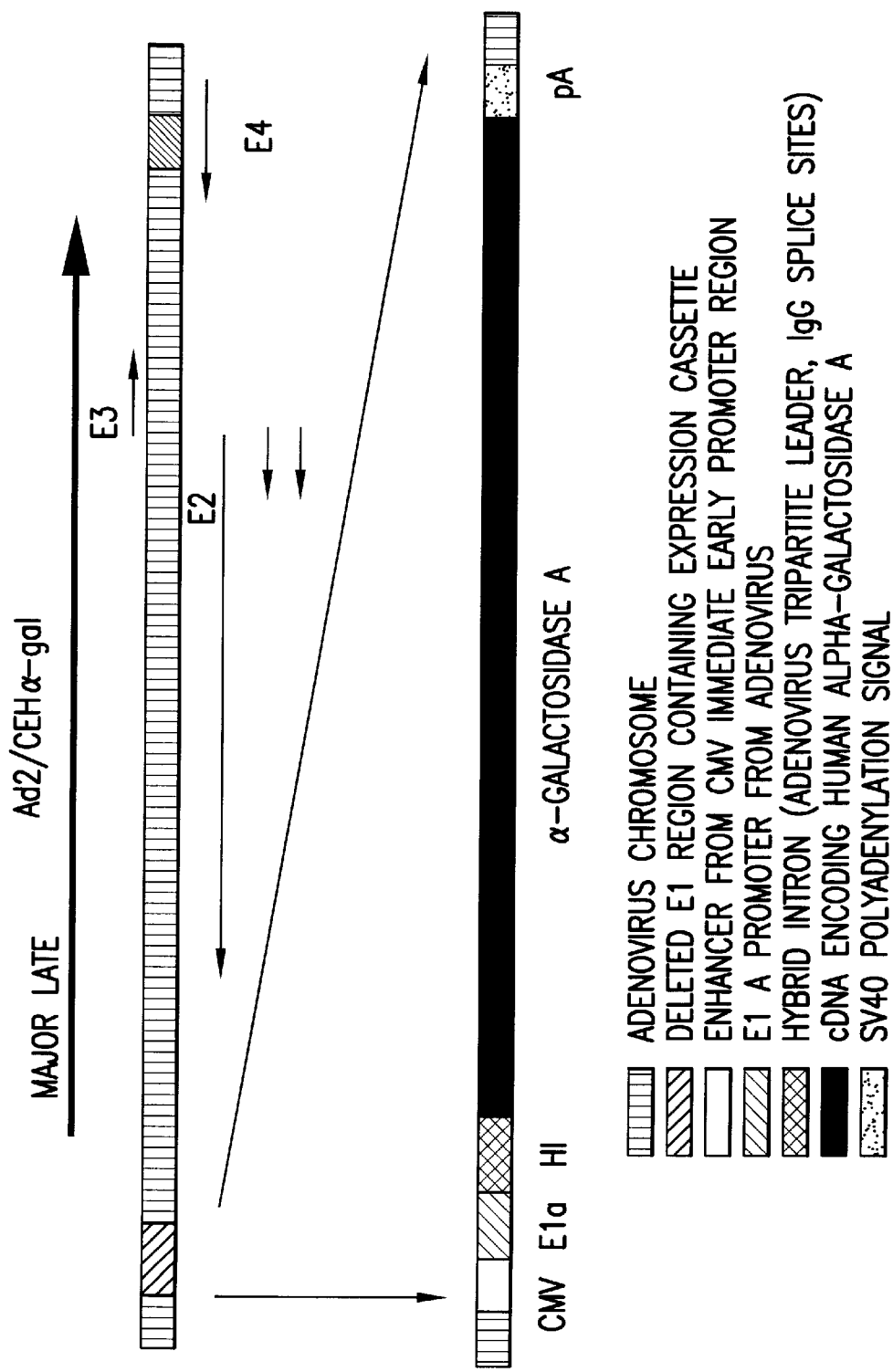
FIG. 2 shows the adenovirus expression vector Ad2/CEHα-gal.

Ad2/CEHα-gal The E1-deleted adenovirus expression vector using an Ad2 serotype viral backbone was constructed as provided in U.S. Pat. No. 5,670,488, the disclosure of which is incorporated herein by reference. The E1 region of the virus genome was deleted to allow space for an expression cassette. Deleting the E1 region also makes the virus incapable of replication. The adenovirus E1 promoter was used to drive expression of the human α-galactosidase A cDNA. The hybrid intron was included after the promoter. The polyadenylation signal was taken from the SV40 virus. (FIG. 2).

Example 2

Uptake of Human α-galactosidase A Produced from Ad2/CEHα-gal by Fabry Fibroblasts Human primary cells were infected with Ad2/CEHα-gal at the following MOIs (Fabry fibroblast cell line GM02775: 0, 2, 4, 6 and 8 µU α-gal/µg protein; skeletal muscle cell line SkMC: 0, 0.5, 1, 1.5, 2, 2.5 and 3 µU α-gal/µg protein). Three days after infection conditioned culture medium was collected and filtered to remove virus particles. Filtered conditioned medium was applied to uninfected Fabry fibroblasts (GM02775). After a five hour incubation, medium was removed, cells were washed with PBS, and harvested in 0.5 ml lysis buffer. Fibroblasts from normal (GM02770B) and Fabry donors which had not been exposed to conditioned medium were harvested and assayed as controls. Cell lysates were assayed using the fluorescent substrate 4-methylumbelliferyl-α-D-galactopyranoside (4-mu-α-gal). (FIGS. 3A and 3B). The assays showed that human primary cells infected with Ad2/CEHα-gal secreted biologically active α-galactosidase A that was taken up by Fabry fibroblasts.

Example 3

Tissue Distribution of α-galactosidase A in Normal vs. Fabry's Knockout Mice

Normal (C57BL/6n) and Fabry knockout mice (provided by Dr. Robert Desnick, Mount Sinai School of Medicine, New York, N.Y.) were assayed for levels of α-galactosidase A using the 4-mα-α-gal activity assay. A full body perfusion was performed at the time of sacrifice and the organs were harvested and stored at −80° C. Tissues were homogenized in assay buffer and put through several freeze-thaw cycles. Fabry mice showed significantly reduced levels of α-galactosidase A activity when compared to normal mice in all organs tested. (FIG. 4).

Example 4

Tissue Distribution of α-galactosidase A after Intranasal, Intravenous and Intramuscular Administration of pCFA-hAGA pCFA-hAGA, complexed with the cationic lipid GL-67 ($N^4$-spermine cholesteryl carbamate), disclosed, e.g., in U.S. Pat. No. 5,783,565, incorporated herein by reference, was administered to C57BL/6n mice. α-gal levels in tissue homogenates were assayed by an enzyme-linked immunosorbant assay (ELISA) specific for human α-galactosidase. Intranasal instillations were performed using 100 µl of GL-67: DOPE(1:2):pCFA-hAGA complex at a 0.6 mM:3.6 mM lipid:DNA ratio. See, for example, International Publication No. WO 96/18372 (Cationic amphiphiles and plasmids for intracellular delivery of therapeutic molecules, e.g.,GL-67); Fasbender, A. J. et al.,*Am. J Physiol.* 269(1) Pt 1: L45–51 (1995); Zabner, J. et al., *J. Biol. Chem.* 270(32) :18997–19007 (1995). Animals were sacrificed 2 days post-instillation. Intravenous injections were performed with 100 μl of GL-67: DOPE:DMPE-PEG (1:2:0.005): pCFA-hAGA complex at a 4 mM:4 mM lipid:DNA ratio into the tail vein. These animals were sacrificed 2 days post-administration.

Figure 5:
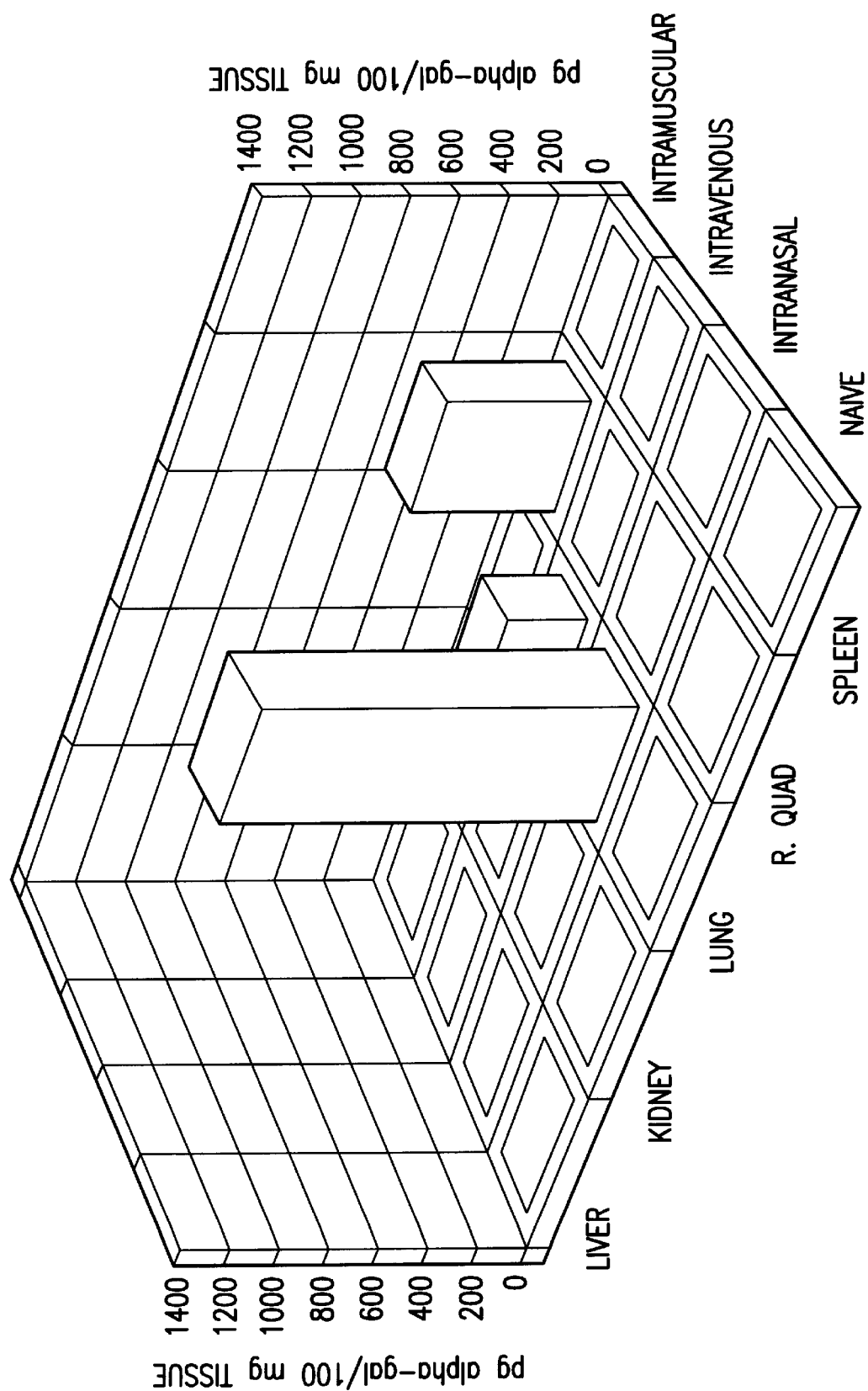
FIG. 5 shows tissue distribution of α-galactosidase A after intranasal, intravenous and intramuscular administration of plasmid.

Intramuscular injections of 100 μg of naked pCFA-hAGA in 50 μl were delivered into the right quadriceps muscle group. These animals were sacrificed 5 days post-administration. Enzyme was detectable in the tissues primarily transfected by the chosen lipid/DNA formulations and routes of delivery. (FIG. 5).

Example 5
Tissue Distribution of α-galactosidase A in Fabry Knockout Mice after Administration of Ad2/CEHα-gal Virus was injected into the tail vein of female Fabry's knockout mice at a dose of $5 \times 10^9$ IU in 260 μl. Mice were sacrificed after 3 days. The ELISA was used to detect levels of α-galactosidase A activity in various organs. Intravenous injections of virus resulted in high levels of α-galactosidase A in all organs tested (10–100 fold). The wide distribution of enzyme activity makes this a promising therapy for Fabry's Disease. (FIG. 6A).

Virus was injected into the right quadriceps muscle group of female Fabry's knockout mice at a dose of $9.5 \times 10^8$ IU in 50 μl. These mice were sacrificed after 5 days. An ELISA was used to detect levels of α-galactosidase A in various organs. Intramuscular injections of virus resulted in significant levels of enzyme at the site of injection, as well as moderate enzyme levels in liver and spleen, indicating that infected cells at the injection site secreted enzyme that was taken up by cells in other tissues. (FIG. 6B).

Figure 7B:
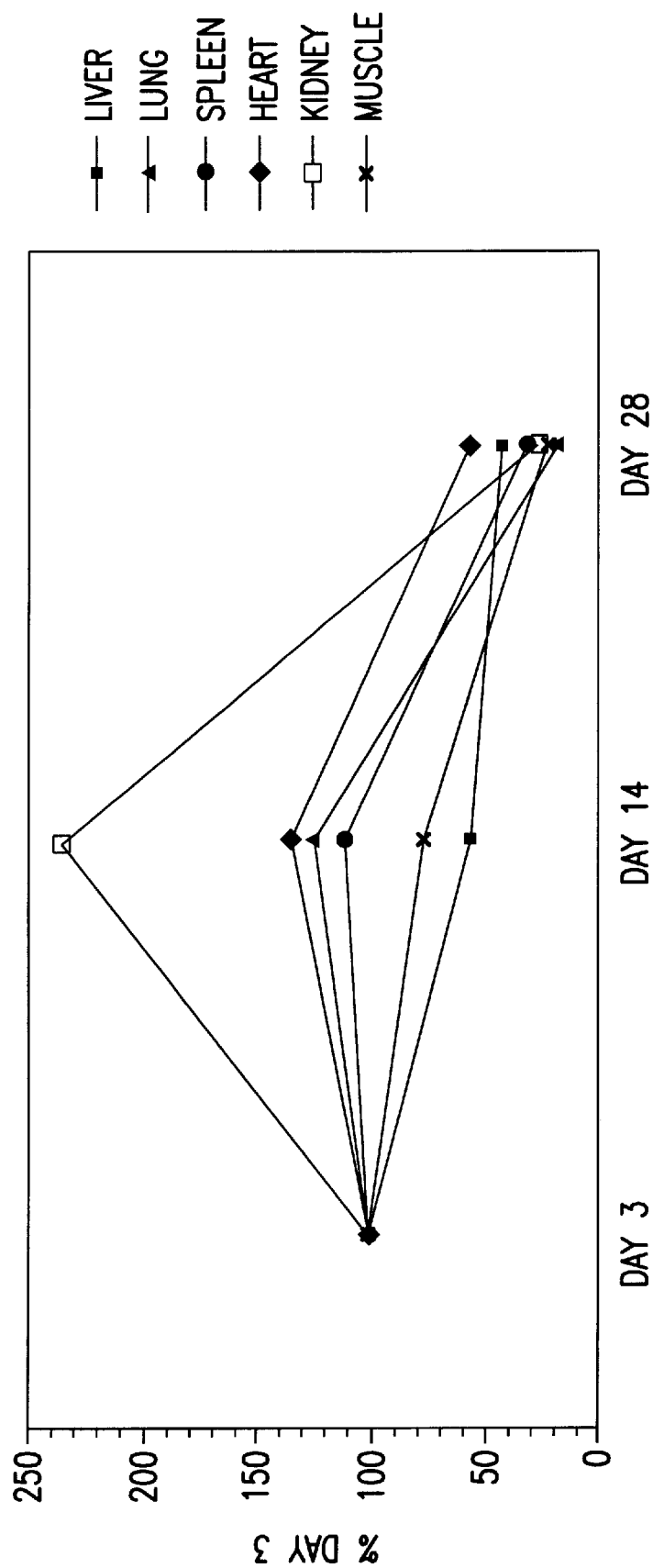

Example 6
Time Course of α-galactosidase A Expression after Intravenous Injection of Ad2/CEHα-gal into C57BL/6n Mice The present experiment showed that significant levels of active enzyme persisted for some time after administering the vector. Virus was injected into the tail vein of C57BL/6n mice. The dose delivered was $5 \times 10^9$ IU in a volume of 260 μl. Organs were harvested after 3, 14 and 28 days. An ELISA was used to detect α-galactosidase A levels in tissue homogenates. (FIGS. 7A and 7B). By day 28, the levels of enzyme had dropped ~5 –10 fold from day 3 levels, however the levels were still significantly higher than wild-type levels.

Figure 8A:
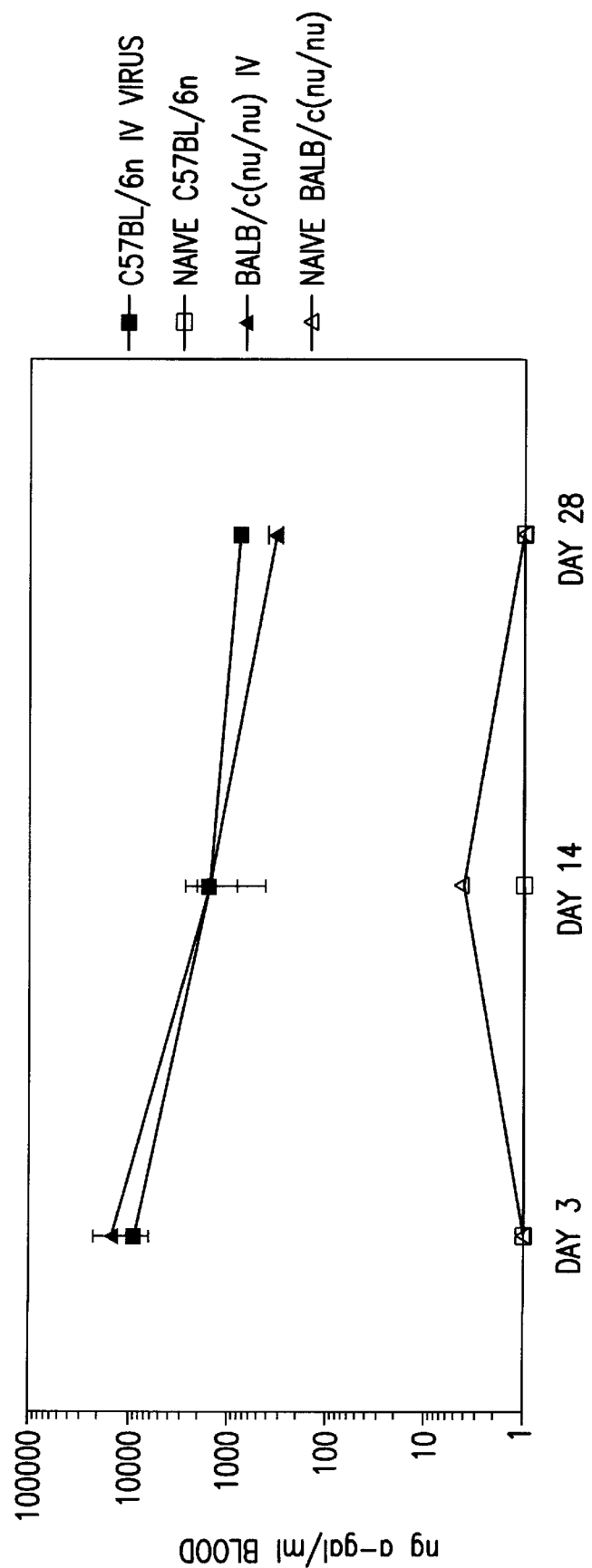

Example 7
Levels of α-galactosidase A in Whole Blood after Intravenous Injection of Ad2/CEHα-gal into C57BL/6n and BALB/c(nu/nu)mice Virus was injected into the tail vein of C57BL/6n or BALB/c(nu/nu) mice. The dose delivered was $5 \times 10^9$ IU in a volume of 260 μl. Blood was harvested after 3, 14 and 28 days. An ELISA was used to detect α-galactosidase A levels in whole blood. (FIGS. 8A and 8B). The presence of α-galactosidase A in blood indicated secretion of enzyme into the bloodstream from sites of infection. The levels of enzyme dropped ~10 fold by 14 days. The similar pattern in nude and normal mice implies that this decrease is not due to an immune response.

Example 8
Short Term Time Course Showing Reduction of GL3 levels in Fabry Mice Intravenously Administered Ad2/CEHα-gal.

Female Fabry mice between 3 and 8 months of age (n=12, for each group) were injected via the tail vein with a high dose ($1.65 \times 10^{11}$ particles) or a low dose ($1.65 \times 10^{10}$) of Ad2/CEHα-gal in 0.25 ml PBS/5% sucrose. The mice were sacrificed at 3, 7 or 14 days post injection (n=4 per time point per dose). Two naive female Fabry mice (3 months and 8 months of age) were sacrificed on day 3 for reference for GL3 levels in untreated mice. A blood sample was collected at the time of sacrifice to measure α-galactosidase A activity. Upon sacrifice, the animals were perfused with PBS and various organs collected. The organs were divided into two parts, one to assay for α-galactosidase A activity via an ELISA specific for human α-galactosidase A and the other extracted and assayed for GL3 using an ELISA-type assay specific for GL3. The data were normalized to the weight of the tissue sample.

Figure 9A:
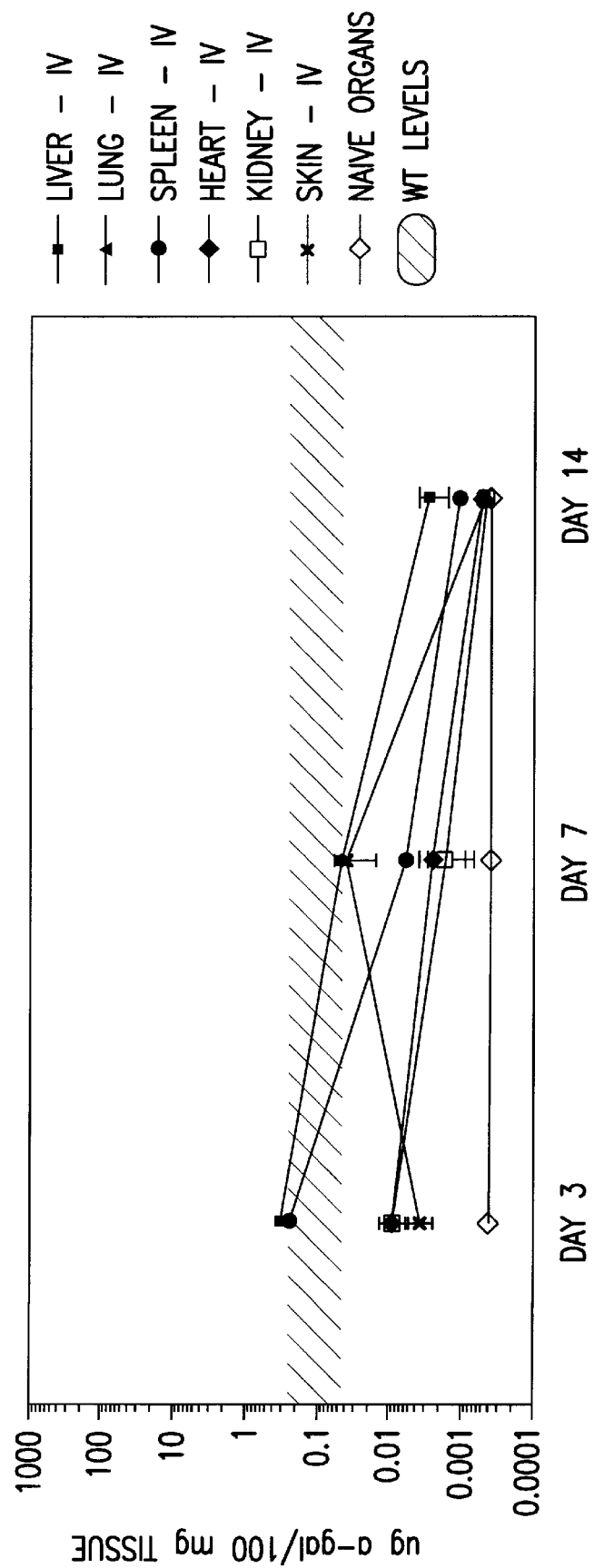
FIGS. 9A–9B show levels of α-galactosidase A in tissues of Fabry mice after intravenous injection of a low level dose ($1.65\times10^{10}$ particles) of Ad2/CEHα-gal.
Figure 9B:
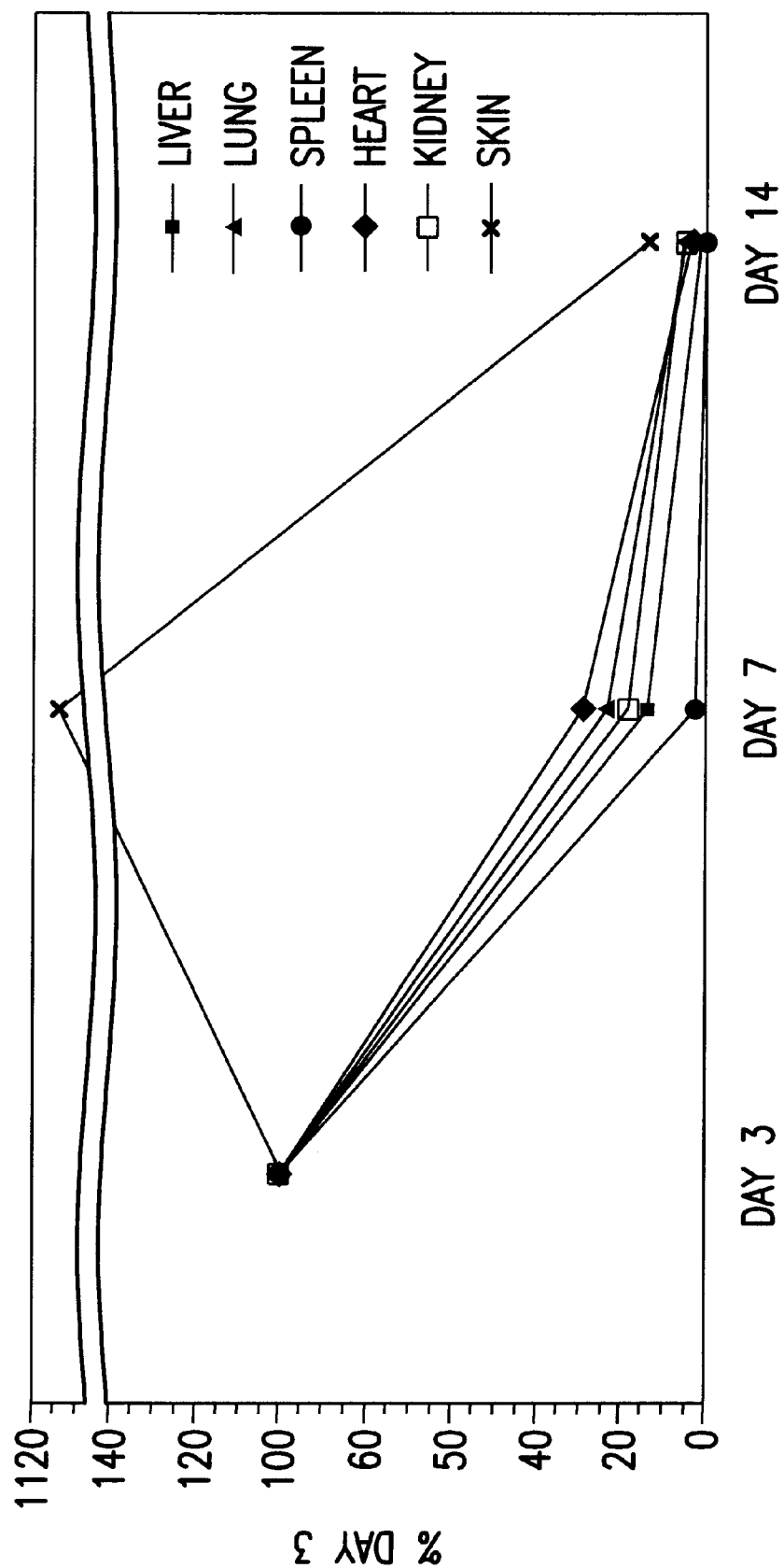
Figure 10A:
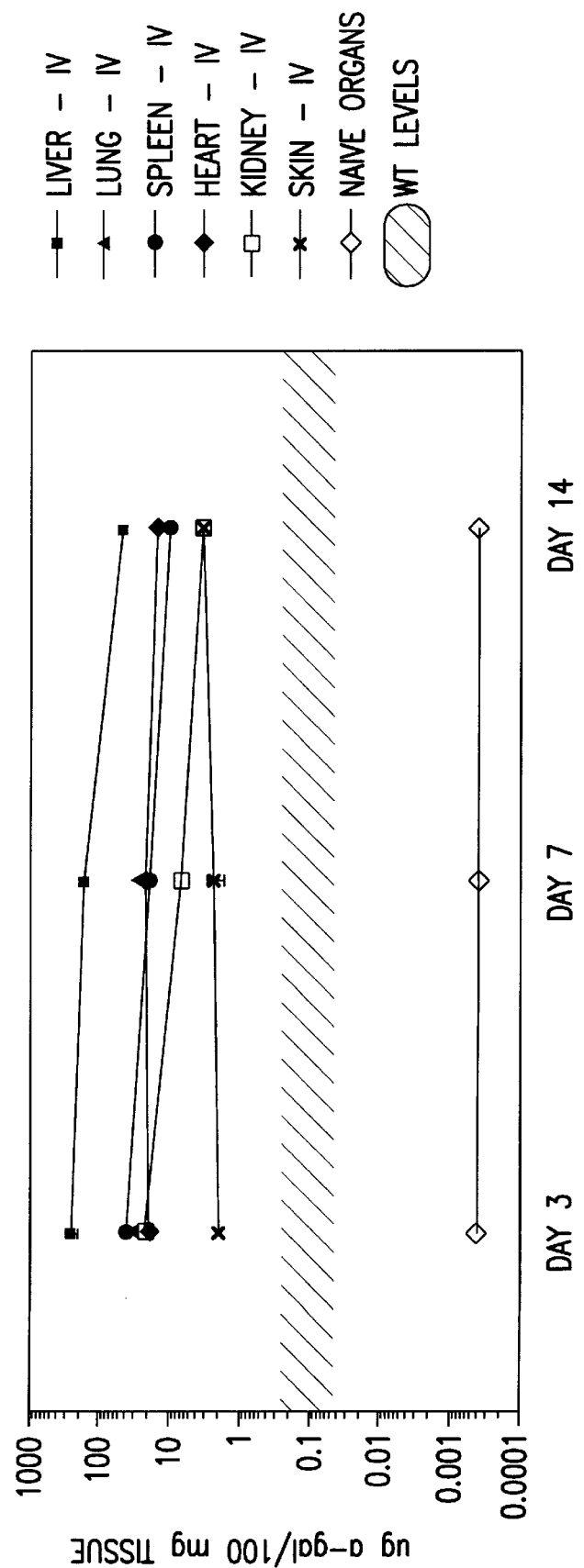
FIGS. 10A–10B show levels of α-galactosidase A in tissues of Fabry mice a intravenous injection of a high level dose ($1.65\times10^{11}$ particles) of Ad2/CEHα-gal.
Figure 10B:
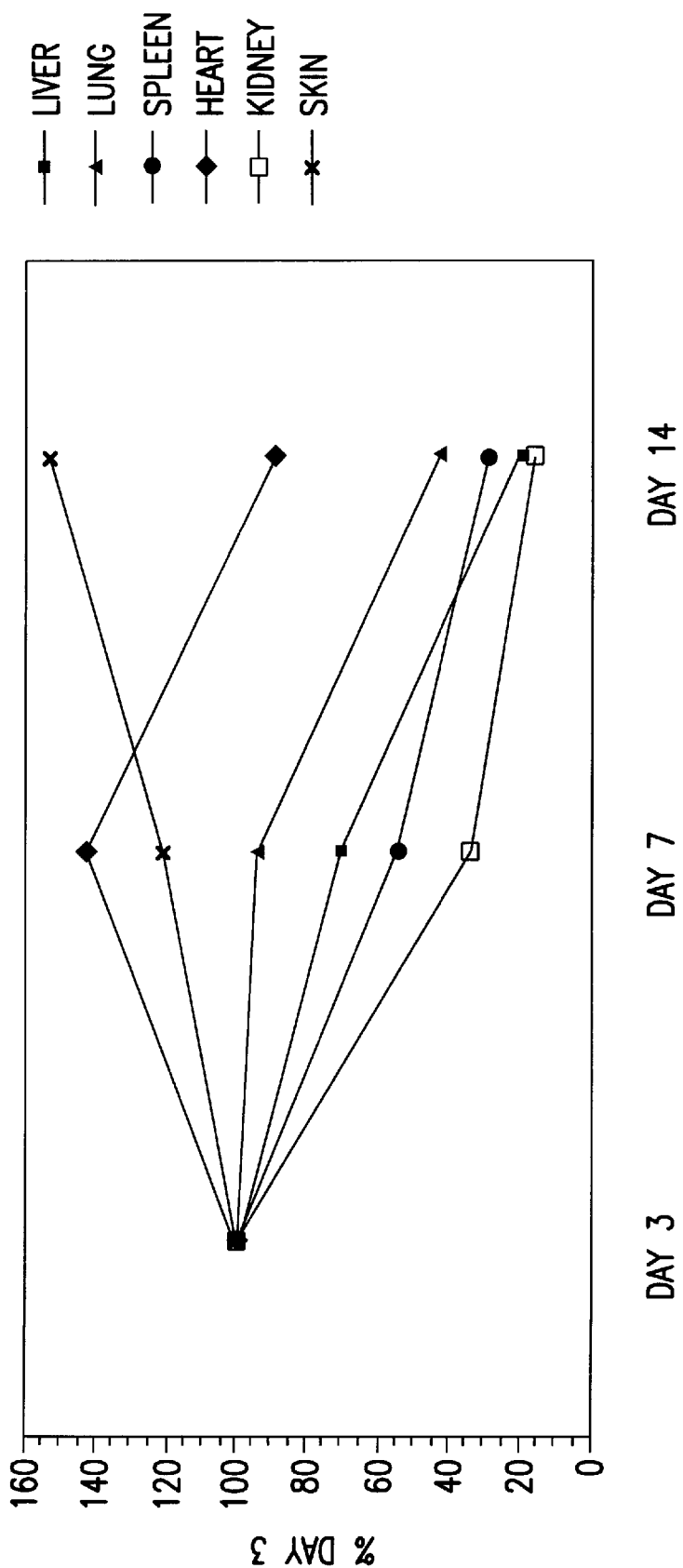
Figure 11A:
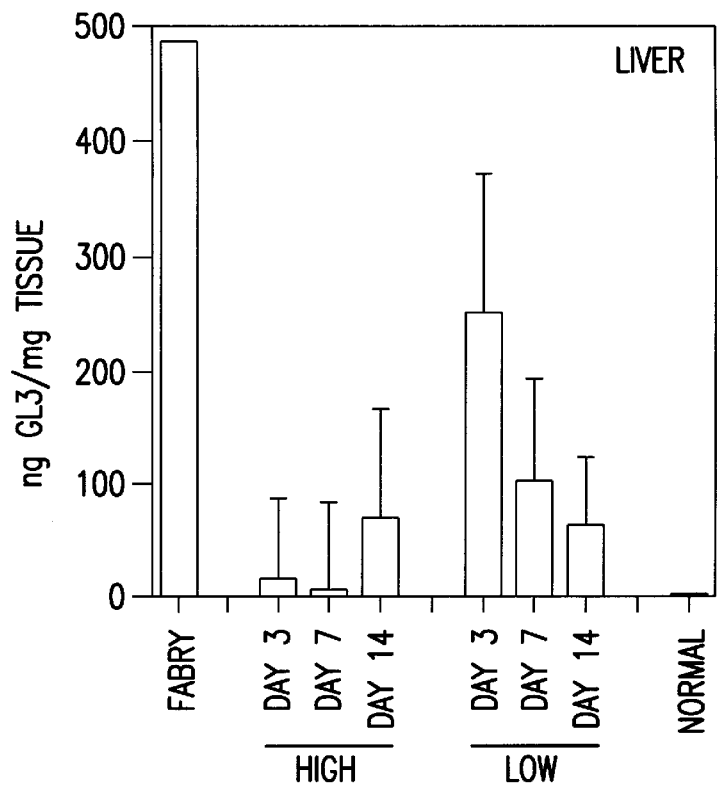
FIGS. 11A–11F show levels of GL3 in Fabry mouse tissues after intravenous injection of high and low doses of Ad2/CEHα-gal over time.
Figure 11B:
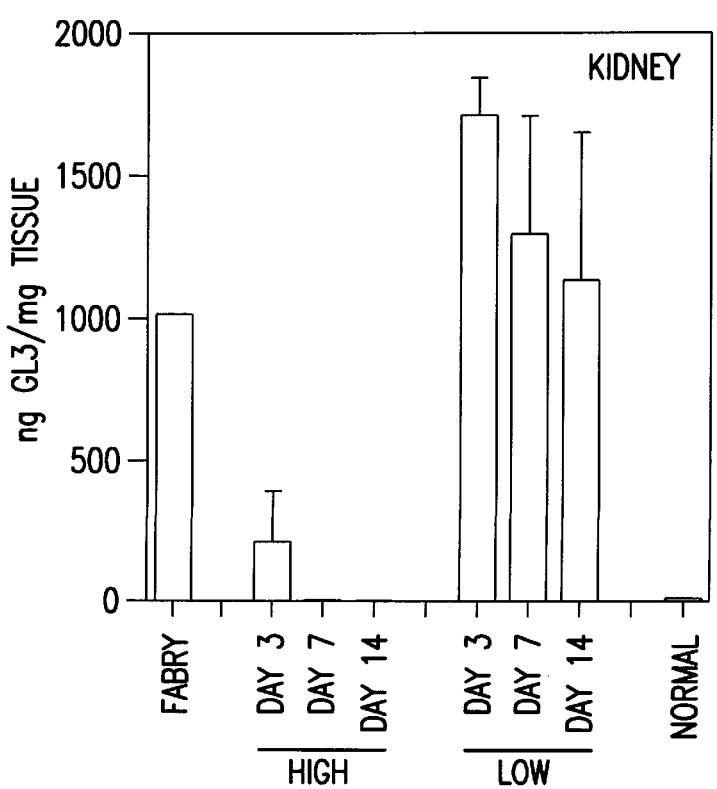
Figure 11C:
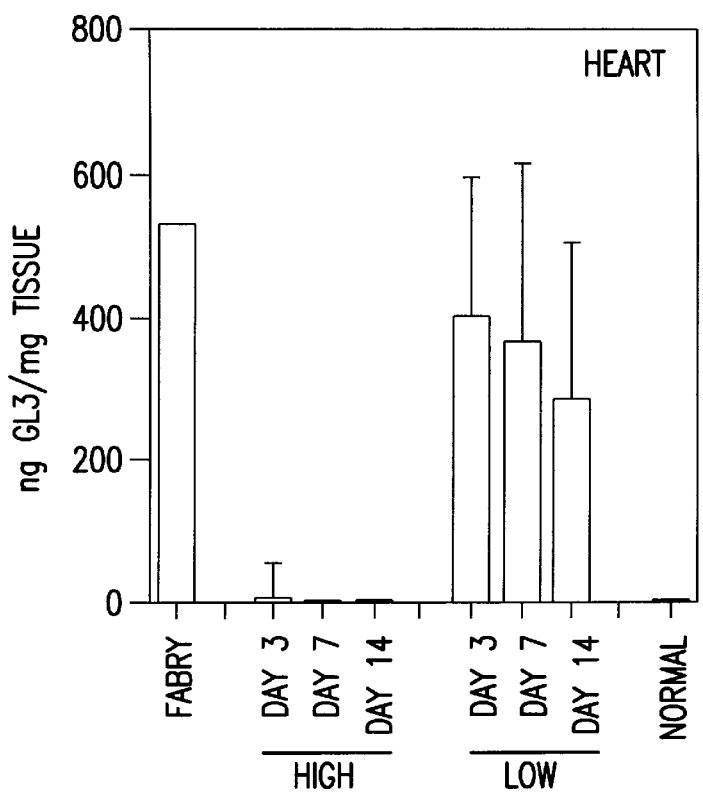
Figure 11D:
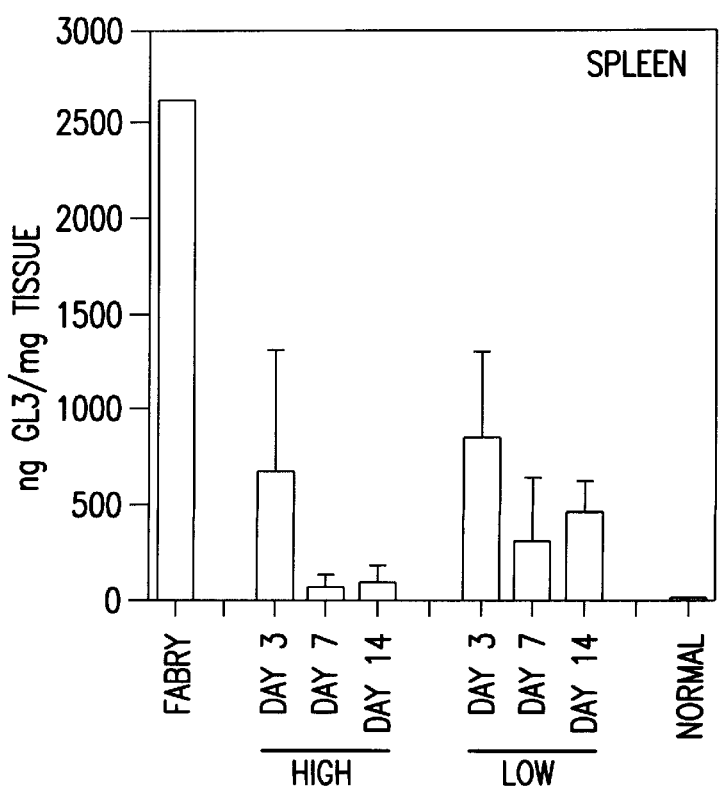
Figure 11E:
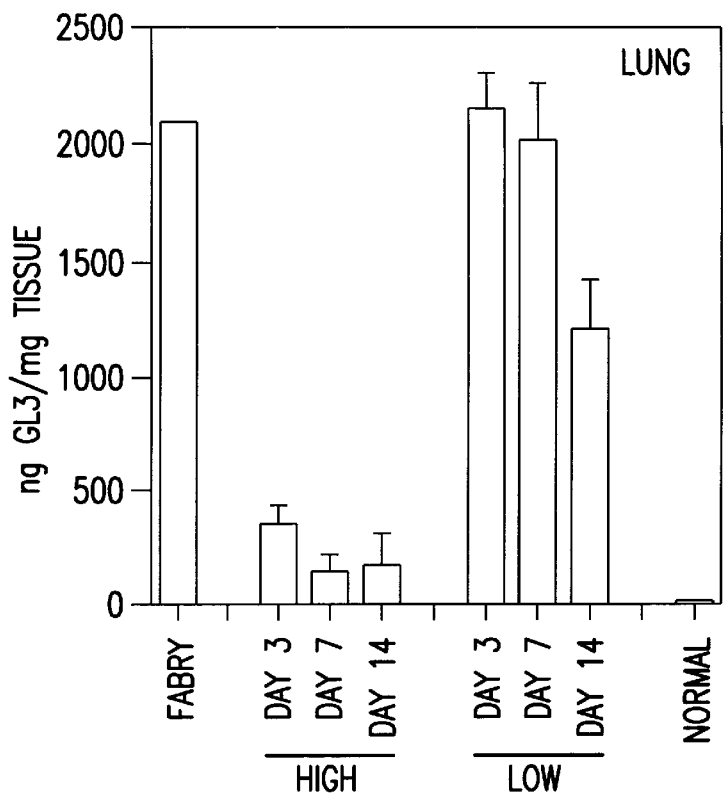
Figure 11F:
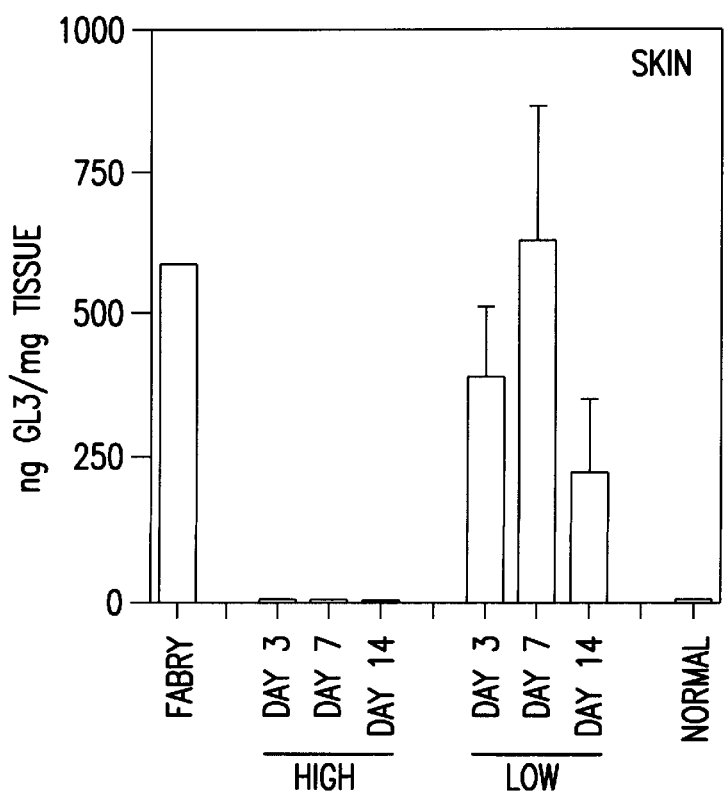

The time course of α-galactosidase A activity in sampled tissued following low dose and high dose administration of Ad2/CEHα-gal are shown in FIGS. 9A and 10A, respectively. The persistence of α-galactosidase A activity relative to day 3 for each dose is shown in FIGS. 9B and 10B, respectively. This study showed that the high dose of vector produced a many fold increase in α-galactosidase A activity in all tested tissues, relative to naive mice, that persisted for up to 14 days. There was a modest increase in α-galactosidase A activity at the lower dose.

Concurrent with the increase in α-galactosidase A levels in the tested tissues was a significant decrease in GL3 levels in all tissues at the high doses of vector (FIG. 11). The lower drop in GL3 levels following the low dose of vector is believed to be an artifact based on the age of the tested animals. The low dose studies used younger mice that have lower amounts of stored GL3 than older mice. For example, studies at Mount Sinai School of Medicine in New York have shown that Fabry mice accumulate GL3 in their tissues over time. At 3 months, the GL3 levels are significantly above normal, climbing to about twice the 3 month level in 5 month old mice. Between 5–11 months, the GL3 levels stabilize, with the 5 months GL3 level being about 80% of the maximum. All of the high dose studies were performed in 5–7 month old mice, so the initial GL3 levels would not vary so much in this group.

Example 9
Repeat Administration of Adenovirus to Mice Following Immunosuppression using Deoxyspergualin (DSG)

Because repeat administration of an adenoviral vector containing the α-galactosidase A gene may be required to sustain α-galactosidase A levels in treated individuals, various immunosuppressants may be used to inhibit an immune response to the administered adenovirus vector. Such immune responses can inhibit the effectiveness of readministered virus. The present experiment shows the effect of the immunosuppressant agent DSG on repeat adenovirus administration.

Two groups of four BALB/c mice were treated with $1 \times 10^{11}$ particles of Ad2/CFTR-16 (an E1 deleted, partially E3 deleted vector capable of persistent transgene expression as disclosed in PCT/US98/07840 filed Apr. 14, 1998, the disclosure of which is incorporated herein by reference) via tail vein injection (high dose). Two groups of four mice received $1 \times 10^{10}$ particles of the virus (low dose). One group given each dose received 20 mg/kg of DSG via IP injection on days —1 through 5 relative to virus administration. This treatment regime was repeated after 28 days. On day 56 the mice received the same dose of virus, this time using Ad2/CEHα-gal. On day 56 two additional groups of mice received $1 \times 10^{11}$ or $1 \times 10^{10}$ particles of Ad2/CEHα-gal without any prior treatment. Blood was collected from these animals on day —1, 27, and 55 relative to initial virus administration. Three days after they received the Ad2/

Figure 12:
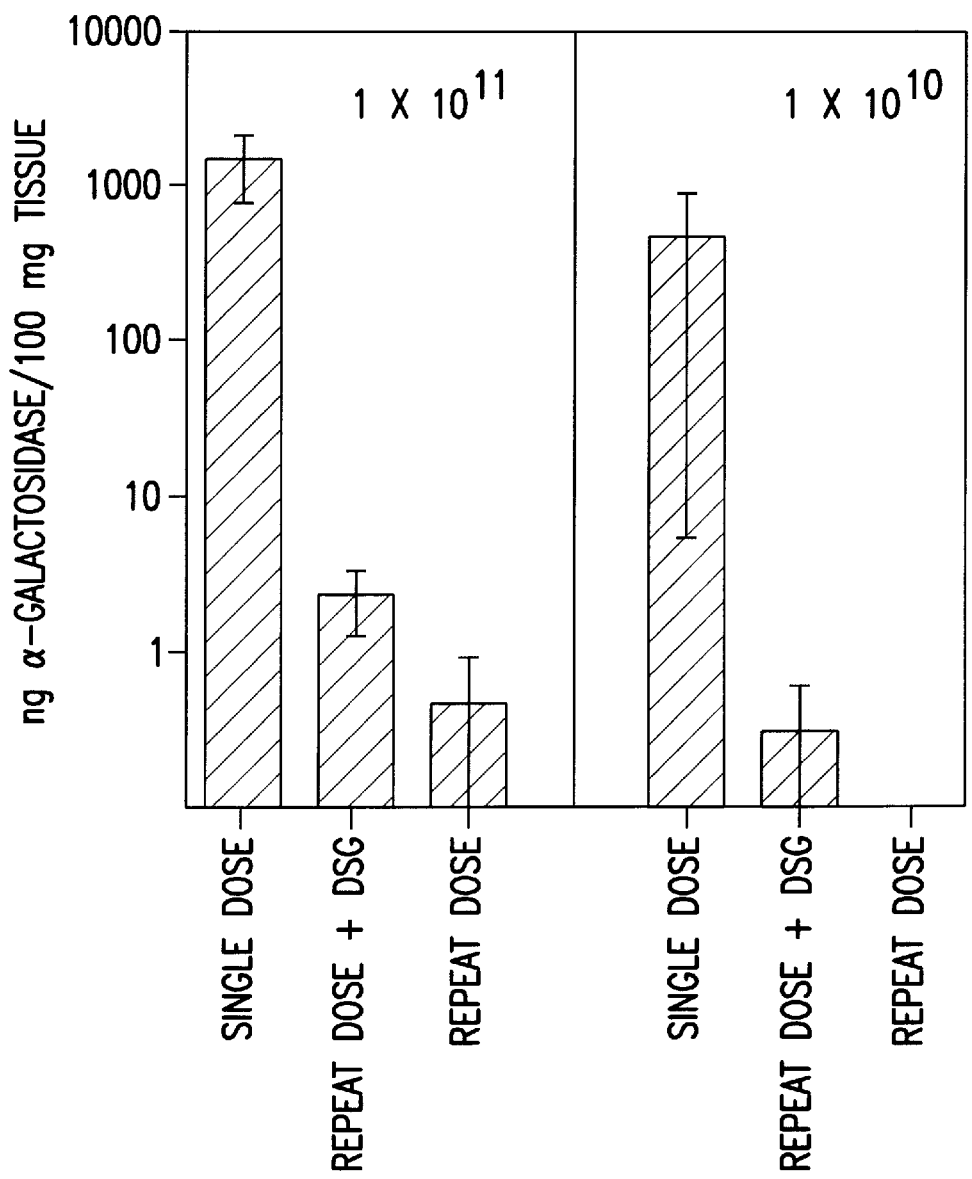
FIG. 12 shows effect of DSG on α-galactosidase A levels in mice after repeat administration of adenovirus vector.
Figure 13:
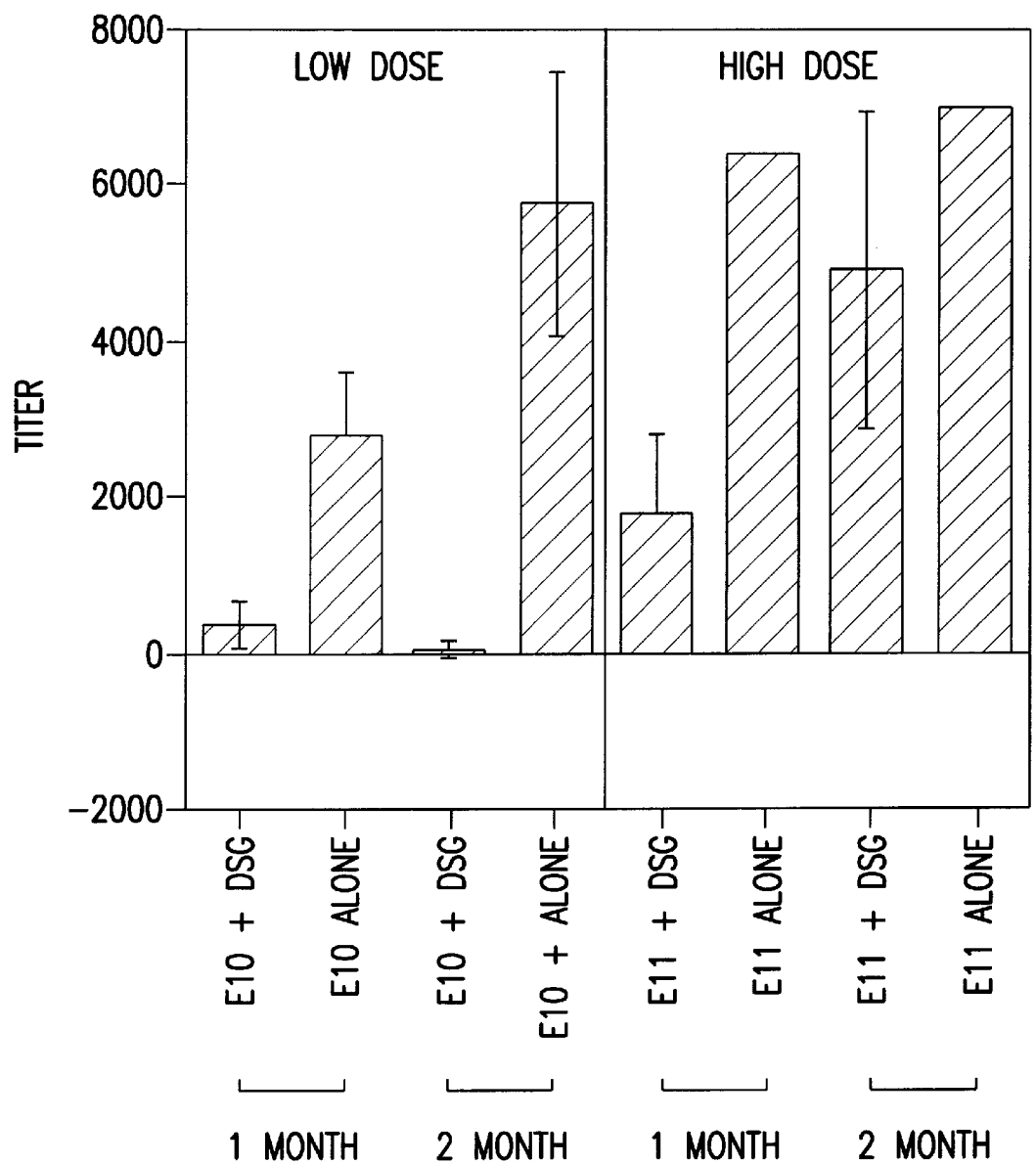
FIG. 13 shows effect of DSG on anti-adenovirus antibody levels in mice following repeat administration of adenovirus vector.

CEHα-gal virus, the animals were sacrificed and organs collected. Tissue homogenates were analyzed for α-galactosidase A expression using an ELISA specific for human α-galactosidase A. Antibodies made to adenovirus were titred from plasma samples. With both dosage levels of virus, α-galactosidase A levels were higher in the mice given DSG then those not receiving DSG (FIG. 12), indicating that DSG was beneficial in obtaining transgene expression upon repeat viral administration. Likewise, DSG inhibited anti-adenovirus antibody titers in mice (FIG. 13).

Example 10
Efficacy of Repeat Adenovirus Administration to Mice Following Immunosuppression with Anti-CD154 (CD40 Ligand) Antibody (MR1)

The MR1 antibody, obtained from PharMingen (Catalog No. 090205), reacts with gp39 (CD40 Ligand—CD154), an accessory molecule expressed on activated T lymphocytes. Noelle et al., *Proc. Natl. Acad. Sci. USA* 89:6550 (1992); Roy et al., *J. Immunol.* 151:2497 (1993). gp39 is required for an immune response to be mounted; inhibition thereof with MRI inhibits immune responses. Indeed, antibody to gp39 (CD40 Ligand; CD154) has been shown to inhibit both human and cellular immune response, facilitating repeated administration of adenovirus to mouse airway. See Scaraia et al., *Gene Therapy* 4:611(1997); WO 98/08541, incorporated herein by reference.

The present experiment was designed to show the effectiveness of MR-1 in inhibiting an immune response to repeat adenovirus administration in mice.

Figure 14:
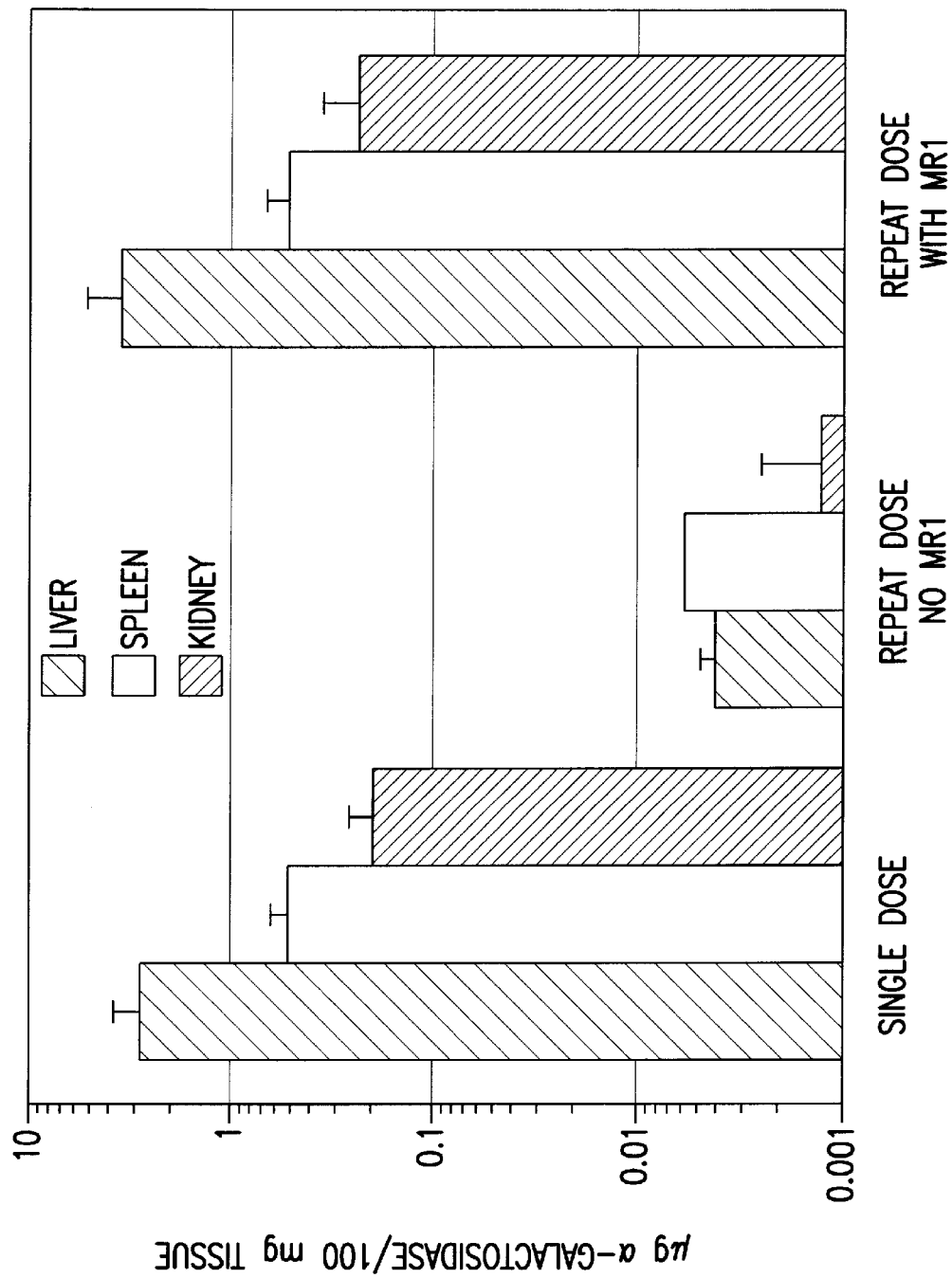
FIG. 14 shows the effect of MRI antibody directed to CD154 on α-galactosidase A levels in mouse tissues following repeat administration of adenovirus vector.

Two groups of three BALB/c mice were administered $1\times10^{11}$ particles of Ad2/CFTR-16 via tail vein injection. One group of mice received 500 μg of MR1 anti-CD154 antibody via intraperitoneal injection days —1, 1, 4, 7, and 14 relative to virus administration. Twenty eight days after the first virus administration the mice received a second injection of $1\times10^{11}$ virus particles, this time using Ad2/CEHα-gal/CEHα-gal. A third group of three mice only received the Ad2/CEHα-gal injection on day 28. Three days after the second virus injection animals were sacrificed and organs harvested. Tissue homogenates were analyzed for α-galactosidase A expression using the ELISA. As shown in FIG. 14, this experiment showed that it was possible to attain high levels of α-galactosidase A transgene expression with a second administration of adenovirus following short term immunosuppression with MR1 antibody.

We claim:

1. A method for providing biologically active human α-galactosidase A to cells of an individual having deficiency in biologically active human α-galactosidase A, said method comprising in vivo administration into cells competent for the production of biologically active human α-galactosidase A of a vector comprising and expressing a DNA sequence encoding biologically active human α-galactosidase A, wherein the vector is taken up by the cells competent for the production of biologically active human α-galactosidase A, the DNA sequence is expressed therein and biologically active human α-galactosidase is produced.

2. A method according to claim 1, wherein the cells harboring the vector secrete biologically active α-galactosidase A which is taken up by other cells deficient in α-galactosidase A.

3. A method according to claim 1 wherein the vector is a viral vector.

4. A method according to claim 3 wherein the viral vector is adenovirus.

5. A method according to claim 1 wherein the vector is a plasmid.

6. A method according to claim 5 wherein the plasmid is complexed with a cationic lipid.

7. A method according to claim 4 wherein the adenovirus is complexed with DEAE-dextran.

8. A method for providing biologically active human α-galactosidase A to cells of an individual with Fabry disease comprising in vivo administration into the cells of a Fabry individual an amount of Ad2/CEHα-gal effective to transfect and sustain expression of biologically active α-galactosidase A in cells deficient therein.

9. A method according to claim 8 wherein Ad2/CEHα-gal is complexed with DEAE dextran.

10. A method according to claim 8 wherein the expressed α-galactosidase A is secreted from the infected cells and is taken up by other cells deficient therein.

11. A method for providing biologically active α-galactosidase A to the cells of an individual with Fabry disease comprising in vivo administration into the cells of a Fabry individual an amount of pCFA-hAGA effective to transfect and sustain expression of biologically active α-galactosidase A in cells deficient therein.

12. A method according to claim 11 wherein pCFA-hAGA is complexed with a cationic lipid.

13. A method according to claim 12 wherein the cationic lipid is $N^4$-spermine cholesteryl carbamate.

14. A method according to claim 11 wherein the expressed α-galactosidase A is secreted from the cells harboring said vector and is taken up by other cells 20 deficient therein.

* * * * *